017
United States Patent [19]

Asato

[11] 4,036,979

[45] July 19, 1977

[54] COMPOSITIONS CONTAINING 4,5,6,7-TETRAHYDROBENZ[B]THIEN-4-YL-UREAS OR DERIVATIVES AND METHODS OF ENHANCING GROWTH RATE

[75] Inventor: Goro Asato, Titusville, N.J.

[73] Assignee: American Cyanamid Company, Stamford, Conn.

[21] Appl. No.: 676,252

[22] Filed: Apr. 12, 1976

Related U.S. Application Data

[63] Continuation-in-part of Ser. No. 572,492, April 25, 1975, abandoned, which is a continuation-in-part of Ser. No. 436,826, Jan. 25, 1974, abandoned.

[51] Int. Cl.² ............................................. A61K 31/38
[52] U.S. Cl. .............................. 424/275; 424/248.51; 424/258; 424/263; 424/267; 424/274

[58] Field of Search ................... 424/275, 248.51, 258, 424/274, 263, 267; 260/332.2 R, 332.2 A

[56] References Cited

U.S. PATENT DOCUMENTS

| 2,623,824 | 12/1952 | Gaudry | 424/319 |
| 3,793,452 | 2/1974 | Strong et al. | 424/275 |

*Primary Examiner*—Leonard Schenkman
*Attorney, Agent, or Firm*—Edward A. Conroy, Jr.

[57] ABSTRACT

This disclosure describes a novel method for improving feed efficiency and accelerating the growth rate of veterinary homothermic animals by administering to said animals a growth-promoting amount of a cycloalkano[b]thien-4-ylurea or thiourea.

76 Claims, No Drawings

COMPOSITIONS CONTAINING 4,5,6,7-TETRAHYDROBENZ[b]THIEN-4-YL-UREAS OR DERIVATIVES AND METHODS OF ENHANCING GROWTH RATE

CROSS REFERENCE TO RELATED APPLICATIONS

This application is a continuation-in-part of my abandoned application Ser. No. 572,492, filed Apr. 25, 1975 which is a continuation-in-part of my abandoned application Ser. No. 436,826, filed Jan. 25, 1974.

SUMMARY OF THE INVENTION

This invention relates to a method for improving feed efficiency and enhancing the growth rate of veterinary homothermic animals such as poultry, fur-bearing, and farm animals by orally or parenterally administering to said animals a growth-promoting amount of cycloalkano[b]thien-4-ylurea or thiourea which may be represented by formula (I) below:

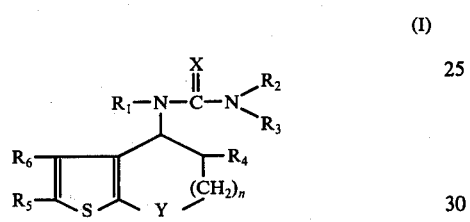

(I)

wherein X is divalent oxygen or divalent sulfur; Y is a divalent moiety of the formulae:

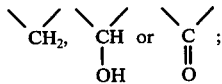

$n$ is the integer 1 or 2; $R_1$ is hydrogen or alkyl $C_1$-$C_4$; $R_3$ is hydrogen, alkyl $C_1$-$C_4$, cycloalkyl $C_3$-$C_6$, allyl, 2-propynyl, benzyl or β-phenylethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substitutents listed in Table I below:

TABLE I $R_2$ hydrogen
alkyl $C_1$-$C_{12}$
cycloalkyl $C_3$-$C_6$
allyl
methallyl
2-butenyl
2-propynyl
hydroxy
alkoxy $C_1$-$C_6$
allyloxy
methallyloxy
2-butenyloxy
methoxymethyl
—O—CH$_2$—COOH
phenoxy
benzyloxy
—CH$_2$—CH$_2$—OH
—CH$_2$—CH$_2$—O—CH$_3$
—CH$_2$—CH$_2$—S—CH$_3$
—CH$_2$—CH(OR)$_2$
—CH$_2$—CF$_3$
—CH$_2$—CN
—CH$_2$—CO$_2$R
—NH—CO$_2$R
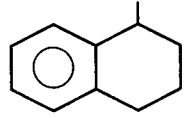

TABLE I-continued $R_2$

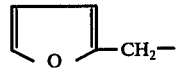
—CO$_2$C$_2$H$_5$
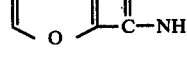
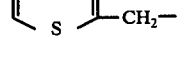
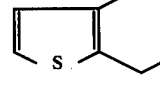
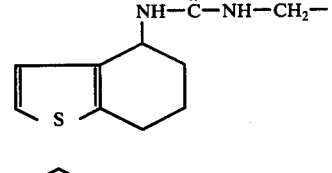
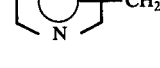
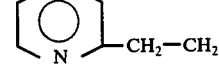
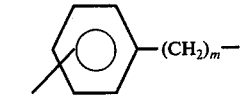

wherein (in Table I) R is alkyl $C_1$-$C_4$, $m$ is 0, 1 or 2, and Q is selected from the group consisting of the substituents listed in Table II below:

TABLE II

| | Q | |
|---|---|---|
| m = 0 | m = 1 | m = 2 |
| 2-methyl-4-bromo | hydrogen | hydrogen |
| 3,4-methylenedioxy | 4-chloro | |
| 3- or 4-methoxy | 4-methoxy | |
| 4-ethoxy | 3,4-methyl-enedioxy | |
| 4-chloro | | |
| 4-butoxy | | |
| 4-methylthio | | |
| 2,4-dimethyl | | |
| 2,5-dimethoxy | | |
| 2,4-dichloro | | |
| 4-nitro | | | and $R_2$ and $R_3$ taken together with the associated N(itrogen) is selected from the group consisting of morpholino, piperidino, pyrrolidino, 4-phenylpiperazino, 4-(4-methoxyphenyl)-piperazino, 4-carbethoxypiperazino, 4-oxopiperazino, 1,2,3,4-tetrahydroquinolino and the moiety of the formula:

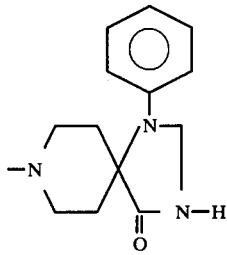

DETAILED DESCRIPTION OF THE INVENTION

A preferred embodiment within the scope of the present invention may be represented by the following formula:

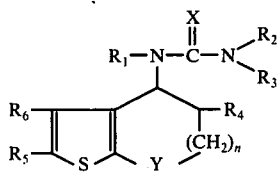

(II)

wherein X, Y, n, $R_1$, $R_3$, $R_4$, $R_5$ and $R_6$ are as hereinabove defined and $R_2$ is selected from the group consisting of the substituents listed in Table III below:

TABLE III
$R_2$
hydrogen
alkyl $C_1$-$C_8$
cycloalkyl $C_3$-$C_6$
allyl
methallyl
2-butenyl
2-propynyl
hydroxy
alkoxy $C_1$-$C_6$
allyloxy
methallyloxy
2-butenyloxy
methoxymethyl
phenoxy
—$CH_2$—$CH_2$—OH
—O—$CH_2$—COOH
—$CH_2$—CH(OR)$_2$
—$CH_2$—$CF_3$
—$CH_2$—CN
—NH—$CO_2$R

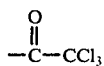

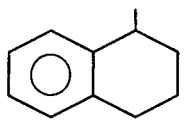

TABLE III-continued
$R_2$

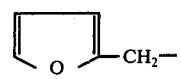

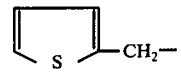

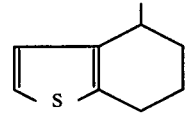

benzyloxy wherein (in Table III) R and m are as hereinabove defined and Q is selected from the group consisting of the substituents listed in Table IV below:

| TABLE IV | | |
|---|---|---|
| | Q | |
| m = 0 | m = 1 | m = 2 |
| 4-chloro | hydrogen | hydrogen |
| 3,4-methylene-dioxy | 4-methoxy | |
| 3- or 4-methoxy | | |
| 4-ethoxy | | |
| 4-butoxy | | |
| 4-methylthio | | |
| 2,4-dimethyl | | |
| 2,4-dichloro | | |
| 4-nitro | | |
| 2-methyl-4-bromo | | |

Another preferred embodiment within the scope of the present invention may be represented by the following formula:

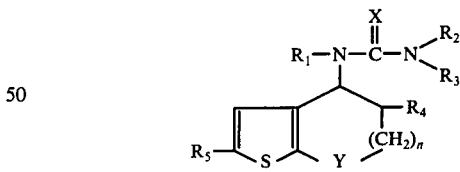

(III)

wherein X, Y, n, $R_1$, $R_3$, $R_4$ and $R_5$ are as hereinabove defined and $R_2$ is selected from the group consisting of the substituents listed in Table V below:

TABLE V
$R_2$
hydrogen
alkyl $C_1$-$C_8$
cycloalkyl $C_3$-$C_4$
allyl
2-propynyl
hydroxy
alkoxy $C_1$-$C_6$
methoxymethyl
phenoxy
4-methoxyphenyl

TABLE V-continued

| $R_2$ |
|---|
| 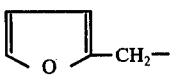 |

Another preferred embodiment within the scope of the present invention may be represented by the following formula:

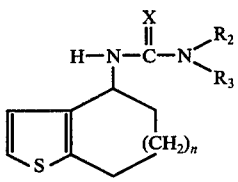

(IV)

wherein X and $n$ are as hereinabove defined and $R_2$ and $R_3$ taken together with the associated N(itrogen) is selected from the group consisting of morpholino, pyrrolidino, 4-phenylpiperazino, 4-(4-methoxyphenyl)-piperazino, 1,2,3,4-tetrahydroquinolino and the moiety of the formula:

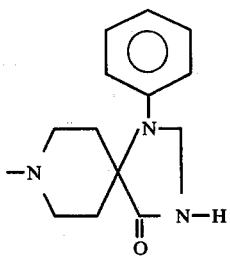

A most preferred embodiment within the scope of the present invention may be represented by the 4,5,6,7-tetrahydrobenzo[b]thien-4-ylureas and thioureas of the following formula:

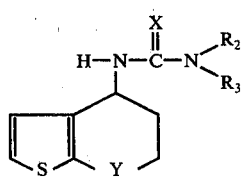

(V)

wherein X and Y are as hereinabove defined, $R_2$ is hydrogen, alkyl $C_1$-$C_8$, allyl, alkoxy $C_1$-$C_4$, 2-propynyl methoxymethyl or hydroxy, and $R_3$ is hydrogen or alkyl $C_1$-$C_4$.

Another most preferred embodiment within the scope of the present invention may be represented by the 5,6,7,8-tetrahydro-4H-cyclohepta[b]thien-4-ylureas and thioureas of the following formula:

(V-a)

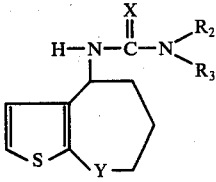

wherein X and Y are as hereinabove defined, $R_2$ is hydrogen, alkyl $C_1$-$C_8$, allyl, alkoxy $C_1$-$C_4$, 2-propynyl, methoxymethyl or hydroxy, and $R_3$ is hydrogen or alkyl $C_1$-$C_4$.

This invention also relates to the use of the enantiomeric ureas and thioureas derived from the resolved cycloalkano[b]thiophen-4-amines for enhancing the growth rate of animals and for improving feed efficiency in the rearing of said animals.

Heretofore, a number of animal growth-promoting agents such as the tetracycline-type antibiotics, penicillin and zinc bacitracin, and hormonal agents such as diethylstilbestrol, have been used successfully to improve feed efficiency and increase the growth rate of poultry and farm animals. However, with the increasing demand for greater food production, skyrocketing animal feed costs and a withdrawal of certain growth-promoting agents from the market place, it is now imperative that new methods and compositions be provided which will enhance the growth rate of animals and improve feed conversion (i.e., the ratio of unit weight of feed consumed per unit weight of gain) in the raising of said animals.

Surprisingly, we have discovered that in veterinary homothermic animals feed efficiency in the raising of poultry, such as chickens and turkeys, fur-bearing animals (i.e., animals raised for their pelts), and farm animals (i.e., livestock such as sheep, cattle, swine and goats) can be improved by orally or parenterally administering to the host animal an effective amount of a cycloalkano [b]thien-4-ylurea or thiourea or the physiologically active optical isomer thereof. We have also found that the administration of said compounds measurably enhances the growth rate of said animals.

In accordance with this invention, the growth rate of veterinary homothermic animals as poultry, fur-bearing and farm animals is measurably improved when a formula (I) cycloalkano[b]thien-4-ylurea or thiourea or its optically active isomer thereof is administered to the above-said host animal in, or with, the feed in an amount equivalent to between 0.0001% and 0.08%, and preferably 0.001% to 0.04% by weight of the feed.

In practice, the active material will generally be formulated as a premix and/or an animal feed supplement which is admixed with a nutritionally balanced feed or added to said feed as top dressing, or the like. Premixes may be prepared by blending about 70% to 99% by weight of rice flour, ground rice hulls, ground corn, or the like, with about 1% to 30% by weight of a formula (I) cycloalkano[b]thien-4-yl-urea or thiourea compound or an optically active isomer thereof.

The growth rate of animals is also improved when a formula (I) cycloalkano[b]thien-4-ylurea or thiourea isadministered as a subcutaneous implant under the skin of the animal. Implants are generally in the form of a paste or pellet which permits the active compound to be released into the bloodstream of the animal over an extended period of time; as for example, from several weeks to several months.

Whether the implant is in the form of a paste or a pellet is a matter of choice. Pellet-type implants which can be used in accordance with this invention may be prepared by admixing from about 50% to 95% by weight of a compound of formula (I) with from about 50% to 5% by weight of a pharmaceutically acceptable carrier such as Castorwax (i.e., glyceryl 12-hydroxystearate), white wax, beeswax, starch, or a high molecular weight (i.e., 4000) polyethylene glycol, or mixtures thereof, alone or in combination with a small amount of a lubricant such as zinc-stearate or magnesium stearate. A small amount of polyvinylpyrrolidone and dibutylphthalate may also be incorporated in the above-said formulations.

Paste implants can be prepared using the same percentages of drug as stated above, but employing a mixture of high molecular weight (i.e., 4000) polyethylene glycol and low molecular weight (i.e., 400) polyethylene glycol alone, or in combination with, Castorwax or beeswax and/or polyvinylpyrrolidone.

Implants may vary in size and weight, but usually range between 10 mg. and 100 mg. per implant. Advantageously, with this method of application, the drug can be administered at periodic intervals throughout the feeding period of the animals. Moreover, formulations and intervals between implantations can be varied to provide a daily drug release of generally about 0.0005 mg. to 0.2 mg. per kg. of body weight, and preferably 0.001 mg. to 0.1 mg. per kg. of body weight.

Typical animal feed supplements and implant formulations are as follows:

Beef Cattle Supplement

|  | Feed Rate | |
| --- | --- | --- |
|  | 2 lbs/Head/Day | 1 lb/Head/Day |
| Dehydrated Alfalfa Meal (17%) | 13.0% | 26.5% |
| Cotton Seed Meal (41%) | 13.5% | 27.0% |
| Limestone (33%) | 11.0% | 22.0% |
| Urea (2.81%) | 6.0% | 12.0% |
| Dried Molasses | 2.5% | 5.0% |
| Salt, Iodized | 2.5% | 5.0% |
| Vitamin-Mineral Premix (1) | 1.0% | 2.0% |
| Drug Premix (2) | 0.5% | 0.5% |
| Ground Corn | 50.0% | — |

(1) Vitamin-Mineral Premix (per 1000 lbs. of supplement)

| | | |
| --- | --- | --- |
| Vitamin A (30,000 I.U./g.) | 833 g. | 1666 g. |
| Cobalt Sulfate ($CoSO_4 \cdot 7H_2O$) | 2 g. | 4 g. |
| Copper Sulfate ($CuSO_4 \cdot 5H_2O$) | 78 g. | 156 g. |
| Manganese Oxide (Mno) | 32 g. | 64 g. |
| Zinc Oxide (ZnO) | 62 g. | 124 g. |
| Elemental Sulfur | 2000 g. | 4000 g. |
| Dehydrated Alfalfa Meal | 1533 g. | 3066 g. |
| | 4540 g. | 9080 g. |

(2) Drug Premix (per 1000 lbs. of supplement)

| Formula (I) Cycloalkano[b]thien- -4-ylurea or thio- urea | Amount in Premix 2 lb. of Supplement/Day | | Amount in Premix 1 lb. of Supplement/ Day | |
| --- | --- | --- | --- | --- |
| Level of Drug per Head/Day (mg.) | Drug (g.) | Ground Corn (g.) | Drug (g.) | Ground Corn (g.) |
| 400 | 200 | 2070 | 400 | 1870 |
| 200 | 100 | 2170 | 200 | 2070 |
| 100 | 50 | 2220 | 100 | 2170 |
| 50 | 25 | 2245 | 50 | 2220 |
| 0 | 0 | 2270 | 0 | 2270 |

Typical Pellet Implant Formulations

| | | Preferred |
| --- | --- | --- |
| (A) | 4,5,6,7-Tetrahydrobenzo[b]thien-4-ylurea (50% to 95%) | 50.0%* |
| | Lubricant (i.e., magnesium stearate) | 0.5%* |
| | Glyceryl 12-Hydroxystearate - QS | |
| (B) | 1-Methyl-3-(4,5,6,7-tetrahydrobenzo[b]thien-4-yl)urea | 60.0% |
| | Polyethylene glycol 4000 | 10.0* |
| | Beeswax - QS | |
| (C) | 1-Methoxy-3-(4,5,6,7-tetrahydrobenzo[b]thien-4-yl)urea | 30.0 mg |
| | Beeswax | 1.0 mg. |
| | Magnesium stearate | 1.5 mg. |
| | Dibutylphthalate | 1.0 mg. |
| | Polyvinylpyrrolidone (10% Solution) - QS | |

Typical Paste Implant Formulation

| | | Preferred |
| --- | --- | --- |
| (A) | 1-Hydroxy-1-methyl-3-(4,5,6,7-tetrahydrobenzo-[b]thien-4-yl)urea (100 mg. to 600 mg.) | 200 mg. |
| | Polyethylene glycol 4000 (30% to 50%) | 40%* |
| | Polyethylene glycol 400 - QS | |

*Percent by weight.

Some of the active compounds of the present invention (VI) may be readily prepared by reacting an appropriately substituted cycloalkano[b]thiophen-4-amine (VII) with an appropriately substituted isocyanate or isothiocyanate (VIII) as set forth in the following reaction scheme:

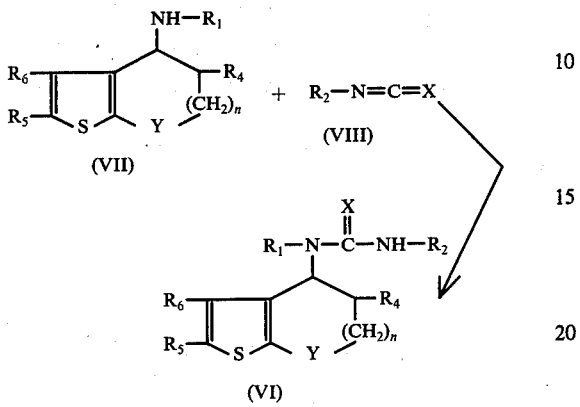

wherein X, Y, $n$, $R_1$, $R_2$, $R_4$, $R_5$ and $R_6$ are as hereinabove defined. The reaction can be carried out using approximately equimolar amounts of the isocyanate or isothiocyanate and the amine or amine acid salt; however, it is generally preferable to employ from 5% to 50% excess of the isocyanate or isothiocyanate wherein the cycloalkano ring does not contain a hydroxyl group. The reaction can be conducted at atmospheric or superatmospheric pressure at a temperature in the range of 0° C. to 100° C., but is preferably conducted at atmospheric pressure at 0° C. to 70° C. in the presence of an organic solvent. Suitable organic solvents include aprotic aromatic solvents such as benzene, toluene, and xylene; chlorinated hydrocarbon solvents such as methylene chloride, chloroform, and dichloroethane; ethers such as tetrahydrofuran, diethyl ether, dimethoxyethane, diethylene glycol dimethyl ether, and dioxane; lower alkyl $C_1$-$C_4$ ketones such as actone, methyl ethyl ketone, methyl butyl ketone, and methyl isobutyl ketone, or mixtures of said solvents.

When the above reaction is carried out using a cycloalkano[b]thiophen-4-amine acid salt, it is desirable to add an acid acceptor to the reaction mixture. Suitable acid acceptors include trialkylamines such as triethylamine, trimethylamine, pyridine or the like; alkali metal carbonates such as sodium and potassium carbonate; alkaline earth metal carbonates such as calcium carbonate; strong basic ion exchange resins; and aqueous alkali in a 2-phase system using an immiscible hydrocarbon solvent such as benzene or toluene, or a chlorinated hydrocarbon such as chloroform or dichloroethane.

Formula (I) cycloalkano[b]thien-4-ylurea or thiourea compounds wherein $R_2$ and $R_3$ are hydrogen may be advantageously prepared from the above-identified amine (VII) or its acid salt by reacting said amine with an approximately equimolar amount of sodium or potassium cyanate or thiocyanate. However, it is generally preferable to employ 5% to 50% excess of the cyanate or thiocyanate wherein the cycloalkano ring does not contain a hydroxy group. The reaction can be conducted under the conditions described above in detail. Suitable solvents include water, polar solvents such as $C_1$-$C_3$ alcohols, tetrahydrofuran, dioxane, ethylene glycol dimethyl ester, diethylene alycol, dimethyl ether, acetone, methyl ethyl ketone and the like and mixtures thereof; in the pH range of 5 to 7 and preferably at pH 6.

Certain of the formula (I) cycloalkano[b]thien-4-ylurea or thiourea compounds (XI) may be readily prepared by reacting approximately equimolar of an appropriately substituted cycloalkano[b]thien-4-yl isocyanate or isothiocyanate (IX) and an appropriately substituted $R_2R_3NH$ amine (X) or its acid-addition salt. The reaction can be graphically illustrated as follows:

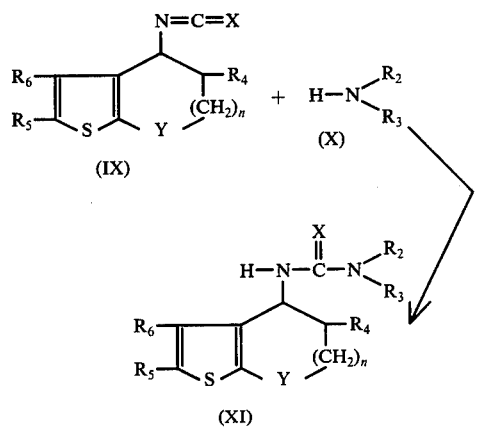

wherein X, Y, $n$, $R_2$, $R_3$, $R_4$, $R_5$ and $R_6$ are as hereinabove defined; with the proviso that Y is not —CHOH. In practice, the reaction is usually conducted with a slight excess (i.e. up to 20% excess) of the amine in the presence of a solvent, such as described above. Although the reaction may be conducted at superatmospheric pressure and temperature as high as 100 ° C., it is generally preferable to conduct the reaction at atmospheric pressure at a temperature between 0° C. and 80° C. When a $R_2R_3NH$ amine acid salt is used it is most beneficial to introduce into the reaction mixture an acid acceptor such as described above. When an aqueous or a $C_1$-$C_3$ alcoholic ammonia or amine solution is used to the above reaction sequence, then the formula (XI) compounds are obtained wherein $R_2$ and $R_3$ are as defined above.

Preparation of the isocyanates (IX) utilized in the above reaction is readily accomplished by reacting the appropriate cycloalkano[b]thiophen-4-amines or their acid salts with phosgene, preferably under anhydrous conditions and under a blanket of inert gas such as nitrogen. The reaction is initially carried out at a temperature between about 0° C. to 40° C., preferably 10° C. to 20° C., and then heated to between about 50° C. and 100° C., and preferably to from 60° C. to 80° C. The reaction is usually also conducted in the presence of an organic solvent such as benzene, toluene or xylene. The isothiocyanates (IX) can be prepared by reacting the appropriate cycloalkano[b]thiophen-4-amines with equimolar amounts of carbon disulfide, triethylamine, and a carbodiimide represented by the formula: G—N=C=N—G where G is cyclohexyl, cycloheptyl, alkyl $C_4$-$C_6$ or the like. This reaction is generally conducted in the presence of a solvent such as tetrahydrofuran or an ether such as diethyl ether, at a temperature between about −10° C. and +25° C. The product can be isolated by distillation or by dry-column chromatography. Alternatively, the formula (IX) isothiocyanates can be prepared by the reaction of 1,1'-thiocarbonyldiimidazole with cycloalkano[b]thiophen-4-amines in the presence of chloroform at ambient temperature.

The reaction of thiocarbonyl diimidazole in the above-mentioned reaction may also lead to the isolation of 1-(1-imidazolyl)-3-(cycloalkano[b]thien-4-yl)thiourea. The analogous reaction also occurs when carbonyl diimidazole is used at room temperature and these reactions may be illustrated as follows:

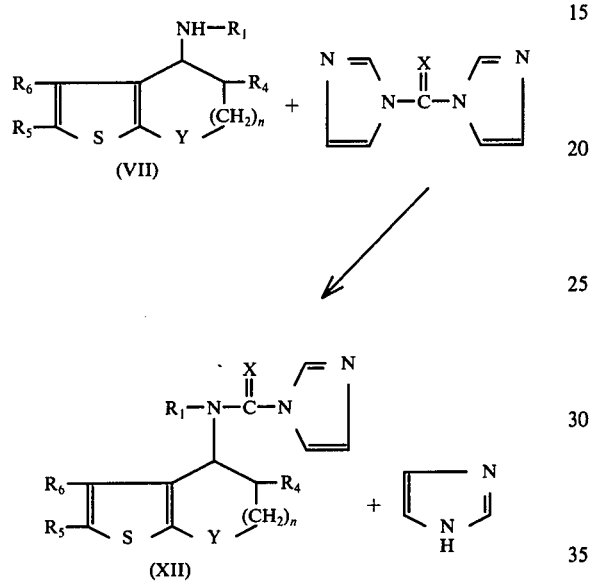

where $R_1$, $R_4$, $R_5$, $R_6$, $n$, $Y$ and $X$ are previously defined. This intermediate (XII) has been discovered to be useful for preparing growth promoting urea compounds especially when the corresponding 4-isocyanate or 4-isothiocyanates of the cycloalkano[b]thiophen-4-amines are difficult to prepare by conventional methods. The reaction may be illustrated as follows:

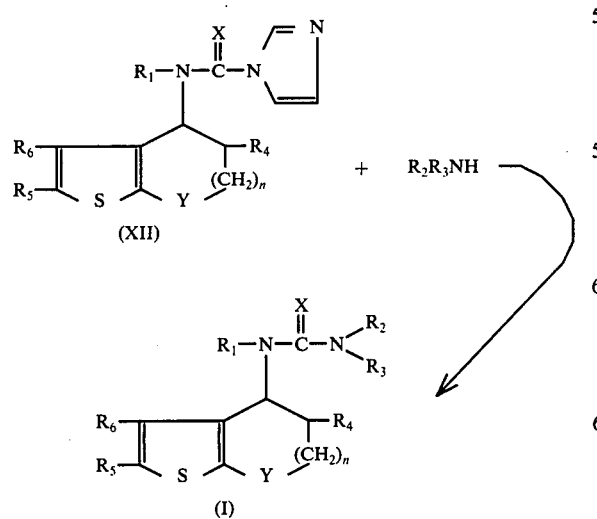

The reaction is run at room temperature to 100° C. and preferably at 25°–50° C. in inert solvents such as chloroform, tetrahydrofuran, methylene chloride and the like.

Advantageously, formula (I) cycloalkano[b]thien-4-ylurea or thiourea compounds wherein Y is carbonyl (XIV) may be readily prepared from the corresponding formula (I) compounds wherein Y is methylene (XIII) by an oxidation reaction as set forth in the following reaction scheme:

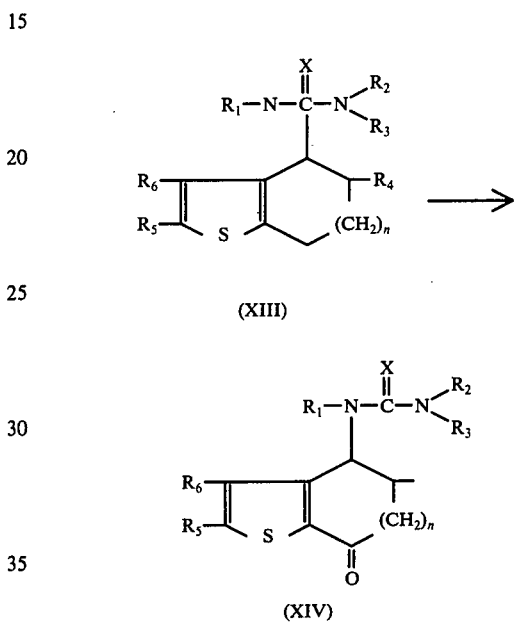

wherein X, $n$, $R_1$, $R_2$, $R_3$, $R_4$, $R_5$ and $R_6$ are hereinabove defined with the proviso that $R_2$ cannot be hydroxyl, or a group containing hydroxyl, or —SCH$_3$, or an aryl- —CH$_3$, or an aryl- or heteroaryl-methylene. The oxidation is carried out by treating a compound of formula (XIII) with a 2 to 8 mole equivalent and preferably with a 4 or 5 mole equivalent of an oxidizing agent selected from the group consisting of ceric ammonium nitrate, silver oxide, or sodium bichromate, at a temperature between about 0° C. and 100° C., and preferably 20° C. to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or the oxidizing agent chromic anhydride in acetic anhydride followed by hydrolysis.

Furthermore, formula (I) cycloalkao[b]thien-4-ylurea or thiourea compounds wherein Y is carbonyl (XVIII) can also be prepared by the above-described oxidative process as set forth in the following reaction scheme:

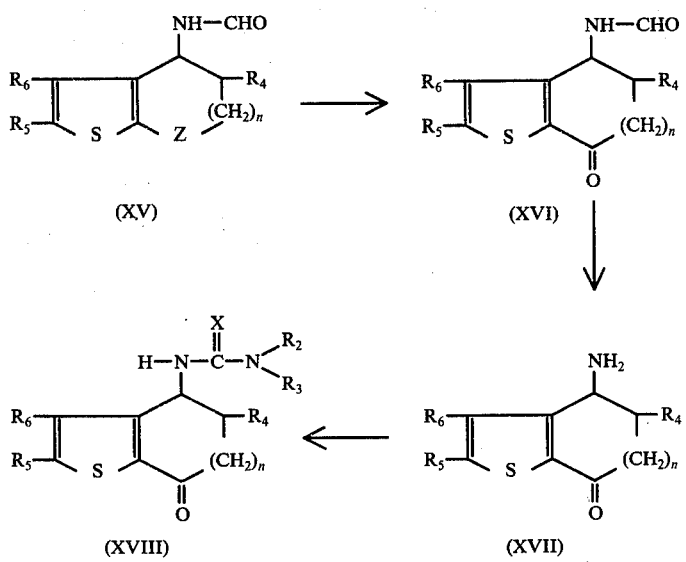

wherein Z is methylene or hydroxymethylene and X, n, $R_2$, $R_3$, $R_4$, $R_5$ and $R_6$ are as hereinabove defined. Upon completion of the oxidation step, the resulting 7-oxo compounds (XVI) are hydrolyzed in dilute mineral acid. The thus-obtained amine (XVII) acid-addition salts are then reacted with an isocyanate or an isothiocyanate at pH 5-7 as hereinbefore described in detail to yield the desired ureas or thioureas (XVIII).

The corresponding 7-hydroxy analogs are prepared from the corresponding formula (I) compounds wherein Y can be only carbonyl by reduction with equimolar or excess amounts of sodium borohydride, at a temperature range between about 0° C. and 75° C., preferably 20°-40° C., in $C_1$-$C_3$ alcohols to afford a mixture of the cis and trans isomers. All of the hereinabove-described processes for the preparation of formula (I) cycloalkano[b]thien-4-ylurea compounds yield racemic (dl) mixtures. The active compounds of the present invention may also be readily prepared by treating an appropriately substituted cycloalkano[b]thiophen-4-amine (VII) with an appropriately substituted carbamoyl or thiocarbamoyl halide (XIX) as set forth in the following reaction scheme:

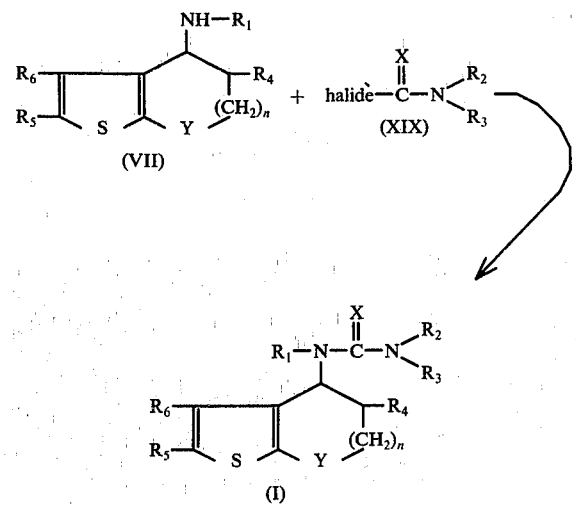

wherein $R_1$, $R_2$, $R_3$, $R_4$, $R_5$, $R_6$, n, X and Y are as hereinabove defined and halide may be chloro or bromo with the proviso that $R_2$ may not be hydroxyl, or a group containing hydroxyl, or a thioether. The free base of (VII) may be employed or an acid-addition salt thereof, preferably the hydrochloride, in the presence of an acid acceptor. Suitable acid acceptors may be pyridine, triethylamine (or any suitable tertiary amine), alkali metal carbonates such as potassium carbonate and sodium carbonate, strong basic ion-exchange resins, and aqueous alkali. The reaction may be run from about room temperature up to about 100° C. and preferably at 25°-50° C. until the desired reaction is complete. The reaction may be carried out under aqueous conditions or in any inert organic solvent such as tetrahydrofuran, dimethoxyethane, and even alcohols. The carbamoyl chloride or thiocarbamoyl chloride is generally used in equivalent amounts but it may be used in excess.

The preparation of the optically active cycloalkano[b]thiophen-4-amine which is a useful intermediate for the synthesis of optically active cycloalkano[b]thien-4-ylureas or thioureas of formula (I) may be accomplished as follows. The racemic (dl) cycloalkano[b]thiophen-4-amine is treated with the (+)-N-benzoylglutamic acid to form a water-insoluble salt of (+)-cycloalkano[b]thiophen-4-amine in high yield. It is not necessary to employ more than one mole of the resolving acid for each two moles of dl amine, as a cheaper acid, preferably acetic acid, can be substituted for the balance of required acid. In this way it is possible to obtain a high yield of the desired (+)-amine based on the resolving acid. The resolved salt, (+)-cycloalkano[b]thiophen-4-amine. (+)-N-benzoylglutamic acid, is treated with alkali which liberates the (+)-amine which separates as an insoluble phase. It can be mechanically separated from the aqueous phase or extracted conventionally with a suitable solvent.

The (—)-amine which remains in solution is then recovered and treated with (—)-N-benzoylglutamic acid and acetic acid in the above-mentioned manner with the molarity adjusted to the amount of (+) amine obtained from the initial resolution. The salt, (—)-cycloalkano[b]thiophen-4-amine (—)-N-benzoylglutamic acid, crystallizes and is then treated in the above-mentioned manner to give the (—)-amine.

With respect to optical isomers, the most preferred optically active ureido and thioureido compounds for enhancement of growth in animals are those which are derived from the (+)-cycloalkano[b]thiophen-4-amine. Thus, the following reaction schemes will exemplify the sequence in the preparation of the optically active compounds.

also a useful intermediate, this compound in its optically active form is desirable. Thus, dl-7-oxo-cycloalkano[b]thiophen-4-amine is readily resolved with (+)-tartaric acid in methanol as follows:

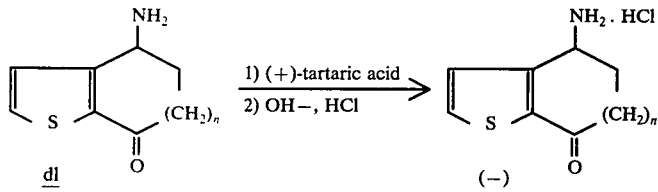

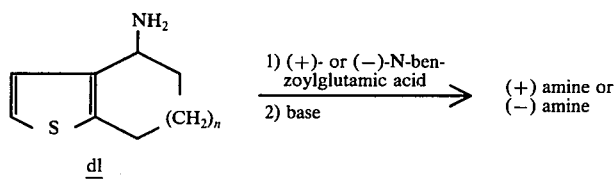

A. 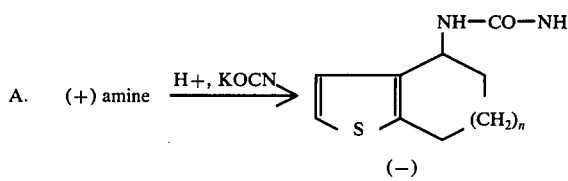

B. 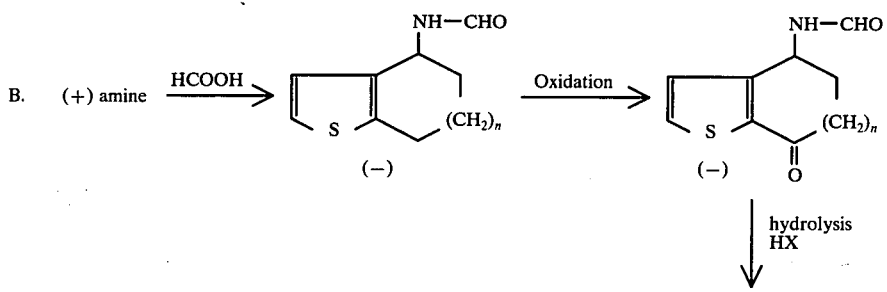

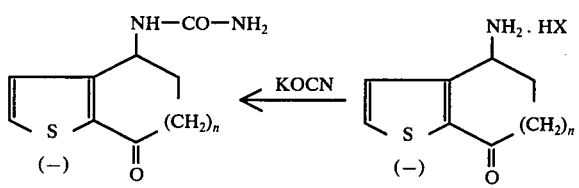

C. 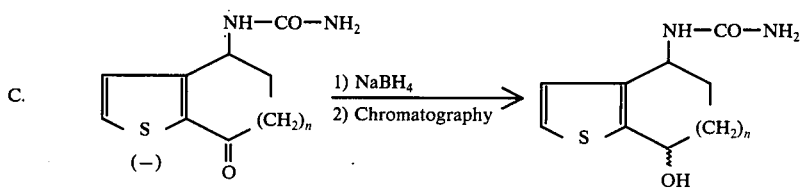

Isomer A (—)
Isomer B (—)

The separation of the cis- and trans-(—)-7-hydroxy-cycloalkano[b]thien-4-ylureas and thioureas is readily achieved by using preparative high-pressure liquid chromatography on silica gel with 1800 ml. of hexane/1000 ml. of CHCl$_3$/425 ml. of MeOH at a flowrate of 40 ml./minute. Since the configurations have not been established, the isomers are designated as Isomer A and Isomer B. Conversely, if (—)-cycloalkano[b]thiophen-4-amine is used in the above sequence, the resulting derivatives of the opposite sign are obtained.

Because 7-oxo-cycloalkano[b]thiophen-4-amine is and the resulting crystalline tartrate salt is recrystallized from 95% ethanol. The salt is decomposed with aqueous NaOH solution and the optically active keto-amine is separated by conventional extraction and acidified with HCl to afford (—)-7-oxo-cycloalkano[b]thiophen-4-amine hydrochloride, which can be used in the manner described above.

The present invention is further illustrated by the preparation of representative examples set forth below, as well as testing data on typical compounds of the invention.

EXAMPLE 1

Preparation of
1-methyl-3-(4,5,6,7-tetrahydrobenzo[b]thien-4-yl)urea

A mixture of 1.89 grams (0.01 mole) of 4,5,6,7-tetrahydrobenzo[b]thiophen-4-amine hydrochloride in 20 ml. of dry benzene is stirred while 1.05 grams (0.01 mole) of triethylamine and 01.7 ml. (excess) of methyl isocyanate are added successively. Addition of the latter gives rise to an exotherm, and the mixture becomes very pasty. The mixture is kept at 45° C. for 1 hour, and after cooling to room temperature, the solid is collected, washed thoroughly with benzene and then with water. On drying, this gives 1.7 grams (81%) of product, melting point 183° C. to 186° C. Recrystallization from acetone gives 1.23 grams, melting point 187.5° C. to 189° C.

On a 0.05 mole scale, the crude yield is 83% (9.15 grams), and the product melts at 181° C. to 186° C. Recrystallization from acetone gives 6.5 grams, melting point 184.5° C. to 187° C.

EXAMPLE 2

Preparation of
1-ethyl-3-(4,5,6,7-tetrahydrobenzo[b]thien-4-yl)urea

In the manner described in Example 1, ethyl isocyanate is allowed to react with 4,5,6,7-tetrahydrobenzo[b]thiophen-4-amine hydrochloride to afford 10.1 grams of 1-ethyl-3-(4,5,6,7-tetrahydrobenzo[b]thien-4-yl)urea. Recrystallization of the crude product from 2-propanol-water (9/1) affords crystals which are dissolved in chloroform and washed successively with 1N sulfuric acid, water and saturated sodium bicarbonate solution. This gives the desired product, melting point 184° C. to 188.5° C. after evaporation of the chloroform.

EXAMPLE 3

Preparation of
1-isopropyl-3-(4,5,6,7-tetrahydrobenzo[b]thien-4-yl)urea

In a nitrogen atmosphere, 5.35 grams of 4,5,6,7-tetrahydrobenzo[b]thiophen-4-amine is stirred in 100 ml. of diethyl ether, and 3.57 grams of isopropyl isocyanate in 40 ml. of diethyl ether is slowly added to afford crystalline product. The mixture is stirred for an additional 0.5 hour and then filtered after standing overnight to give 8.3 grams, melting point 223° C. to 226° C., of 1-isopropyl-3-(4,5,6,7-tetrahydrobenzo[b]thien-4-yl)urea.

EXAMPLE 4

Preparation of
1-(n-hexyl)-3-(4,5,6,7-tetrahydrobenzo[b]thien-4-yl)urea

In the manner described in Example 1, 4,5,6,7-tetrahydrobenzo[b]thiophen-4-amine is allowed to react with n-hexyl isocyanate to give 1-(n-hexyl)-3-(4,5,6,7-tetrahydrobenzo[b]-thien-4-yl)urea, melting point 122° C. to 124° C.

EXAMPLE 5

Preparation of
1-cyclohexyl-3-(4,5,6,7-tetrahydrobenzo[b]thien-4yl-)urea

In a similar manner, as described in Example 1, 4,5,6,7-tetrahydrobenzo[b]thiophen-4-amine hydrochloride is allowed to react with cyclohexyl isocyanate in dry tetrahydrofuran to afford 7 grams of 1-cyclohexyl-3-(4,5,6,7-tetrahydrobenzo[b]thien-4-yl)urea, melting point 222° C. to 225° C.

EXAMPLE 6

Preparation of
1-methoxy-3-(4,5,6,7-tetrahydrobenzo[b]thien-4-yl)urea

A mixture of 5 grams of methoxyamine hydrochloride in 60 ml. of methylene chloride is cooled to about 15° C., and 6 grams of triethylamine in 15 ml. of methylene chloride is added. After 20 minutes, 5.38 grams of 4,5,6,7-tetrahydrobenzo[b]thien-4-yl isocyanate in 20 ml. of methylene chloride is added over 20 minutes at 15° C. to 20° C. After stirring for an hour, the mixture is filtered, and the filtrate is washed with water and then aqueous sodium bicarbonate solution. The solution is dried and evaporated to afford a white solid. The solid is recrystallized from acetone-hexane to afford 5.1 grams, melting point 138.5° C. to 141° C., of 1-methoxy-3-(4,5,6,7-tetrahydrobenzo[b]thien-4-yl)urea.

Similarly, 1-ethoxy-3-(4,5,6,7-tetrahydrobenzo[b]-thien-4-yl)urea and 1-butoxy-3-(4,5,6,7-tetrahydrobenzo[b]-thien-4-yl)urea are prepared by using ethoxyamine hydrochloride and n-butoxyamine hydrochloride, respectively, in place of methoxyamine hydrochloride.

EXAMPLE 7

Preparation of
1-benzyloxy-3-(4,5,6,7-tetrahydrobenzo[b]thien-4-yl)urea

In the manner described in Example 6, O-benzyl hydroxyamine hydrochloride and 4,5,6,7-tetrahydrobenzo[b]thien-4-yl isocyanate are allowed to react to afford 1-(benzyloxy)-3-(4,5,6,7-tetrahydrobenzo[b]thien-4-yl)urea, which is recrystallized from 95% ethyl alcohol-methyl isobutyl ketone. The product melts at 96.5° C. to 99° C.

EXAMPLE 8

Preparation of
1-hydroxy-1-methyl-3-(4,5,6,7-tetrahydrobenzo-[b]thien-4-yl)urea

In the manner described in Example 6, N-methylhydroxylamine hydrochloride and 4,5,6,7-tetrahydrobenzo[b]thien-4-yl isocyanate are allowed to react to afford 1-hydroxy-1-methyl-3-(4,5,6,7-tetrahydrobenzo[b]thien-4-yl)urea, which is recrystallized from acetone-hexane-ether to give crystals, with melting point 98° C. to 102° C.

EXAMPLE 9

Preparation of
1-methoxy-1-methyl-3-(4,5,6,7-tetrahydrobenzo-[b]thien-4-yl)urea

Following the procedure described in Example 6, N,O-dimethyl hydroxylamine hydrochloride and 4,5,6,7-tetrahydrobenzo[b]thien-4-yl isocyanate are allowed to react to give 1-methoxy-1-methyl-3-(4,5,6,7-tetrahydrobenzo[b]thien-4-yl)urea, which is crystallized from acetone-hexane-ether to give product melting at 60° C. to 62.5° C.

EXAMPLE 10

Preparation of 4,5,6,7-tetrahydrobenzo[b]thien-4-ylurea

A mixture of 50 grams of 4,5,6,7-tetrahydrobenzo[b]thiophen-4-amine hydrochloride (about 45 grams real, based on 90% purity) in 100 ml. of water is stirred at about 15° C., and a solution of 23.1 grams of potassium cyanate in 100 ml. of water is added dropwise. After completion of the addition, the mixture is warmed slowly to 70° C. to 75° C. and held for an hour. The mixture is cooled, and the white solid is collected by filtration and washed with water. The solid is air-dried, pulverized, and washed with acetonitrile. On drying, this gives 37.3 grams of crude product, which on treatment with about 1200 ml. of hot acetone gives 11.45 grams, melting point 200° C. to 204° C. of the title compound.

Similarly, 2-methyl- and 3-methyl-4,5,6,7-tetrahydrobenzo[b]thien-4-ylurea are prepared to give products melting at 232°–233° C. and 227°–230° C. (dec.), respectively. When N-methyl-4,5,6,7-tetrahydrobenzo[b]thiophen-4-amine hydrochloride is used, 1-methyl-1-(4,5,6,7-tetrahydrobenzo[b]-thien-4-yl)urea, melting point 151.5–154.5° C., is obtained.

EXAMPLE 11

Preparation of 1-phenethyl-3-(4,5,6,7-tetrahydrobenzo[b]thien-4-yl)urea

A mixture of 3.82 grams of phenethylamine in 100 ml. of diethyl ether under nitrogen atmosphere is allowed to react with 5.38 grams of 4,5,6,7-tetrahydrobenzo[b]thien-4-yl isocyanate in 25 ml. of diethyl ether via dropwise addition of the latter solution. After stirring an hour at room temperature, the mixture is filtered and washed with ether to give 7.9 grams, melting point 163° C. to 166° C., of 1-phenethyl-3-(4,5,6,7-tetrahydrobenzo[b]thien-4-yl)urea.

In a similar manner, methylamine, ethylamine, isopropylamine, n-hexylamine and cyclohexylamine are allowed to react with the aforementioned isocyanate to afford 1-methyl-, 1-ethyl-, 1-isopropyl-, n-hexyl- and 1-cyclohexyl-3-(4,5,6,7-tetrahydrobenzo[b]thien-4-ylurea.

EXAMPLE 12

Preparation of 1,1-dimethyl-3-(4,5,6,7-tetrahydrobenzo[b]thien-4-yl)urea

A solution of 6.27 grams of 4,5,6,7-tetrahydrobenzo[b]thien-4-yl isocyanate in 200 ml. of diethyl ether is charged with gaseous dimethylamine introduced via a capillary tube with stirring. After 0.5 hour of bubbling, the gas flow is terminated, and the mixture is evaporated to dryness to give a solid residue. This is crystallized from acetone-hexane-ether to give 1,1-dimethyl-3-(4,5,6,7-tetrahydrobenzo[b]thien-4-yl)urea melting at 117° C. to 120° C.

The identical product is obtained when 4,5,6,7-tetrahydrobenzo[b]thiophen-4-amine is allowed to react with equivalent amounts (or excess) of dimethylcarbamoyl chloride and triethylamine in dimethylformamide. The reaction mixture is stirred for several hours and then filtered. The filtrate is evaporated to dryness and the residue is purified by crystallization from acetone-hexane to afford the title compound.

EXAMPLE 13

Preparation of 1-benzyl-3-(4,5,6,7-tetrahydrobenzo[b]thien-4-yl)urea

In the manner described in Example 6, except for the use of diethyl ether instead of methylene chloride, 1-benzyl-3-(4,5,6,7-tetrahydrobenzo[b]thien-4-yl)urea is obtained by allowing benzylamine and 4,5,6,7-tetrahydrobenzo-[b]thien-4-yl isocyanate to react. The product melts at 211° C. to 214° C.

The title compound is also obtained by allowing benzyl isocyanate to react with 4,5,6,7-tetrahydrobenzo[b]thiophen-4-amine in ether.

EXAMPLE 14

Preparation of 1-hydroxy-3-(4,5,6,7-tetrahydrobenzo[b]thien-4-yl)urea

The above compound is prepared in the manner described in Example 6, by allowing 4,5,6,7-tetrahydrobenzo-[b]thien-4-yl isocyanate to react with hydroxylamine hydrochloride in the presence of triethylamine. The product melts at 158.5° C. to 160.5° C.

EXAMPLE 15

Preparation of N-(4,5,6,7-tetrahydrobenzo[b]thien-4-yl)-4-morpholinecarboxamide

In the manner outlined in Example 6, except for using diethyl ether instead of methylene chloride, 4,5,6,7-tetrahydrobenzo[b]thien-4-yl isocyanate is allowed to react with morpholine to give N-(4,5,6,7-tetrahydrobenzo[b]thien-4-yl)-4-morpholinecarboxamide, which melts at 152° C. to 154° C.

EXAMPLE 16

Preparation of 2-bromo-4,5,6,7-tetrahydrobenzo[b]thien-4-yl)urea

A sample of 7.84 grams of 4,5,6,7-tetrahydrobenzo-[b]thien-4-ylurea is dissolved in 72 ml. of acetic acid, and 24 ml. of water is added. Bromine (2.3 ml. or 7.05 grams) in 32 ml. of acetic acid is added dropwise. The mixture is stirred at room temperature for 0.5 hour, and then 7.23 grams of sodium acetate in 40 ml. of water is added. An additional 120 ml. of water is added and stirring is continued for 0.5 hour. The white solid is collected, washed with water and cold sodium acetate solution to give 9.8 grams, melting point 206.5° C. to 209.5° C., of 2-bromo-4,5,6,7-tetrahydrobenzo[b]-thien-4-ylurea.

EXAMPLE 17

Preparation of 2-bromo-N-formyl-4,5,6,7-tetrahydrobenzo[b]-thiophen-4-amine

A sample of 54.3 grams of N-formyl-4,5,6,7-tetrahydrobenzo[b]thiophen-4-amine is stirred in 270 ml. of acetic acid and 90 ml. of water. Bromine (53 grams) in 120 ml. of acetic acid is added gradually. After stirring for 0.5 hour at room temperature, 61.5 grams of sodium acetate in 225 ml. water is added. More water is added, and the mixture is extracted with ether. Methylene chloride is added to the ether solution to prevent crystallization, and the solution is evaporated to dryness. The residue is crystallized from acetone-hexane-ether to afford 61 grams, melting point 104° C. to 108° C., of 2-bromo-N-formyl-4,5,6,7-tetrahydrobenzo[b]thiophen-4-amine.

EXAMPLE 18

Preparation of
2-cyano-N-formyl-4,5,6,7-tetrahydrobenzo[b]-thiophen-4-amine

A mixture of 40.9 grams of 2-bromo-N-formyl-4,5,6,7-tetrahydrobenzo[b]thiophen-4-amine, 16.2 grams of cuprous cyanide and 47 ml. of dry dimethylformamide is heated at reflux temperature for 4 hours, and then cooled to about 60° C. and poured into 270 ml. of water. The mixture is extracted with toluene several times, and the toluene extracts are washed with 1.2N hydrochloric acid and saturated sodium chloride respectively. On drying, 5.7 grams of crude product is obtained. The aqueous mother liquor is treated with 97.3 grams of ferric chloride hexahydrate and 30 ml. of concentrated hydrochloric acid and shaken. It is then extracted with toluene several times, and the extracts are washed further with 1.2N hydrochloric acid, saturated sodium bicarbonate solution and brine, respectively. On drying and evaporation of toluene, an additional 2.5 grams of product is obtained. The two crops are combined and recrystallized from acetone-hexane to afford 4.8 grams of 2-cyano-N-formyl-4,5,-6,7-tetrahydrobenzo[b]thiophen-4-amine, melting point 131° C. to 134° C.

EXAMPLE 19

Preparation of
2-cyano-4,5,6,7-tetrahydrobenzo[b]thiophen-4-amine hydrochloride

A mixture of 4.8 grams of 2-cyano-N-formyl-4,5,6,7-tetrahydrobenzo[b]thiophen-4-amine in 70 ml. of 1N hydrochloric acid is refluxed for an hour and evaporated to dryness to afford 4.7 grams of 2-cyano-4,5,6,7-tetrahydrobenzo[b]thiophen-4-amine hydrochloride, melting point 241° C. to 246° C. (dec.).

EXAMPLE 20

Preparation of
2-cyano-4,5,6,7-tetrahydrobenzo[b]thien-4-ylurea

The desired product, 2-cyano-4,5,6,7-tetrahydrobenzo[b]thien-4-ylurea, is prepared in the manner described in Example 10 by allowing 2-cyano-4,5,6,7-tetrahydrobenzo[b]-thiophen-4-amine hydrochloride to react with potassium cyanate. The crude product melts at 210° C. to 214° C., and the product which is recrystallized from nitromethane melts at 209° C. to 213° C.

EXAMPLE 21

Preparation of
2-chloro-4,5,6,7-tetrahydrobenzo[b]thiophen-4-amine

A sample of 11.4 grams 4,5,6,7-tetrahydrobenzo[b]-thiophen-4-amine hydrochloride is stirred in 150 ml. of chloroform at about 10° C., and 6.1 ml. of sulfuryl chloride is added dropwise. The mixture is stirred for 3.5 hours at room temperature, and then about 20 ml. of 50% sodium hydroxide solution is added gradually to dissolve the suspended solid. The mixture is then poured into water and extracted with chloroform twice. The extracts are dried, evaporated to dryness, and the residue is distilled to give 7.4 grams of 2-chloro-4,5,6,7-tetrahydrobenzo[b]thiophen-4-amine, boiling point 94° C. to 98° C/0.5 Torr.

EXAMPLE 22

Preparation of
2-chloro-4,5,6,7-tetrahydrobenzo[b]thien-4-ylurea

The desired product, 2-chloro-4,5,6,7-tetrahydrobenzo[b]thien-4-ylurea, is prepared in the manner described in Example 31 by allowing 2-chloro-4,5,6,7-tetrahydrobenzo[b]thiophen-4-amine to react with hydrocyanic acid in situ. The product melts at 194° C. to 198° C.

EXAMPLE 23

Preparation of
N-(2-acetyl-4,5,6,7-tetrahydrobenzo[b]thien-4-yl)acetamide

N-acetyl-4,5,6,7-tetrahydrobenzo[b]thiophen-4-amine (19.5 grams) is stirred in 300 ml. of methylene chloride in a nitrogen atmosphere, and 17 ml. of acetyl chloride is added. The mixture is cooled to about 10° C., and 28.1 ml. of stannic chloride is added slowly. After stirring for 1.5 hours at room temperature, the mixture is cooled to about 10° C., and 450 ml. of 1.2N hydrochloric acid is added. The mixture is shaken, and the methylene chloride solution is separated and washed with 1N hydrochloric acid, followed by saturated sodium bicarbonate solution. On drying and evaporating to dryness, crystals are obtained. Recrystallization from acetone-hexane gives 15.4 grams, melting point 167.5° C. to 172° C., of N-(2-acetyl-4,5,6,7-tetrahydrobenzo[b]thien-4-yl)acetamide.

EXAMPLE 24

Preparation of
2-acetyl-4,5,6,7-tetrahydrobenzo[b]thiophen-4-amine hydrochloride The product from Example 23 (7.25 grams) is heated with 90 ml. of 1N hydrochloric acid at reflux temperature for 8.5 hours and cooled. The mixture is diluted with water and extracted with methylene chloride. The aqueous layer is then evaporated to dryness using 2-propanol for facilitating removal of water. This gives 4.85 grams of 2-acetyl-4,5,6,7-tetrahydrobenzo[b]thiophen-4-amine hydrochloride.

EXAMPLE 25

Preparation of
2-acetyl-4,5,6,7-tetrahydrobenzo[b]thien-4-ylurea

A sample of 6.3 grams of 2-acetyl-4,5,6,7-tetrahydrobenzo[b]thiophen-4-amine hydrochloride is dissolved in 35 ml. of water and cooled to 15° C. A solution of 2.64 grams of potassium cyanate in 35 ml. of water is added, and after 0.5 hour the mixture is heated at 70° C. for about 40 minutes. The mixture is cooled, and the solid is collected and washed with water. On drying, 5.55 grams, melting point 218° C. to 220° C., of 2-acetyl-4,5,6,7-tetrahydrobenzo[b]thien-4-ylurea is obtained.

EXAMPLE 26

Preparation of
1-ethyl-3-(4,5,6,7-tetrahydrobenzo[b]thien-4-yl)thiourea

A sample of 9.48 grams of 4,5,6,7-tetrahydrobenzo[b]thiophen-4-amine hydrochloride is stirred in 100 ml. of dry tetrahydrofuran, and 6.06 grams of triethylamine is added. After stirring for 15 to 30 minutes, 5.23 grams of ethyl isothiocyanate in 20 ml. of dry tetrahydrofuran is added dropwise, and the mixture is heated for 2 hours at 50° C. The mixture is cooled and filtered, and the filter cake is washed with hexane. The filtrate is evaporated to dryness and poured on ice. The oil is extracted with ether, and the extract is washed with 1N sulfuric acid, water, and saturated sodium bicarbonate solution. The ether extract is dried and evaporated to dryness to afford an oil. This oil crystallizes in ether to afford 1-ethyl-3-(4,5,6,7-tetrahydrobenzo[b]thien-4-yl)thiourea, melting point 106° C. to 112° C.

Similarly, use of methyl isothiocyanate, butyl isothiocyanate and cyclohexyl isothiocyanate affords 1-methyl-, 1-butyl- and 1-cyclohexyl-3-(4,5,6,7-tetrahydrobenzo[b]thien-4-yl)thioureas.

EXAMPLE 27

Preparation of 4,5,6,7-tetrahydrobenzo[b]thiophen-4-amine

A sample (61.2 grams) of 4,5,6,7-tetrahydrobenzo[b]thiophen-4-amine hydrochloride is suspended in 150 ml. of water, and about 400 ml. of 10% aqueous ammonium hydroxide is added to the mixture. The alkaline mixture is then extracted twice with ether, and after drying the ethereal solution is evaporated to dryness. The amine is then distilled to give 40.9 grams, boiling point 100° C. to 102° C. at 3 Torr., of 4,5,6,7-tetrahydrobenzo[b]thiophen-4-amine.

EXAMPLE 28

Preparation of (−)-4,5,6,7-tetrahydrobenzo[b]thiophen-4-ammonium (R)-N-benzoyl glutamate A mixture of 8.04 grams of (R)-(+)-N-benzoyl glutamic acid in 1.92 grams of acetic acid and 80 ml. of water is heated on a steam bath until a solution is obtained. This hot solution is stirred while 9.80 grams of 4,5,6,7-tetrahydrobenzo[b]thiophen-4-amine is added gradually. About 2 ml. of ethanol is used in the transfer as a rinse for the amine. The mixture is then allowed to cool to room temperature and to stand overnight. The mixture is cooled in a refrigerator, filtered to collect the crystals, and the filter cake is washed with water several times. On drying, this gives 9.27 grams of the title salt, melting point 192° C. to 194° C.; $[\alpha]_{589}^{25}$ −9.39°, $[\alpha]_{436}$ −44.6°, $[\alpha]_{365}$ −71.4° at $c = 4.475$ in acetic acid.

The original filtrate is concentrated under reduced pressure to a small volume and partitioned between diethyl ether and aqueous sodium hydroxide. The aqueous base is extracted with ether, and this ether extract is combined with the first ether fraction. This is then dried over magnesium sulfate, evaporated to dryness to afford the recovered amine, and the amine is added to a stirred, hot solution of 8.04 grams of (S)-(−)-N-benzoyl glutamic acid in 1.92 grams of acetic acid and 80 ml. of water. Crystallization occurs rapidly, and after 10 minutes of heating on a steam bath, the mixture is allowed to cool in a refrigerator. The crystals are collected, washed with water and dried to afford 11.1 grams of (+)-4,5,6,7-tetrahydrobenzo[b]thiophen-4-ammonium (S)-N-benzoyl glutamate salt, melting point 192° C. to 193.5° C., $[\alpha]_{589}^{25}$ +12.2°, $[\alpha]_{436}$ + 42.7°, $[\alpha]_{365}$ + 82° at $c = 4.35$ in acetic acid.

EXAMPLE 29

Preparation of (−) 4,5,6,7-tetrahydrobenzo[b]thien-4-ylurea

The salt (8.8 grams of (−)-4,5,6,7-tetrahydrobenzo[b]thiophen-4-amine and (R)-(+)-N-benzoyl glutamic acid is added to ice water mixture in a separatory funnel, and 3.5 grams of sodium hydroxide in 55 ml. of water is added. The mixture is shaken until a solution is obtained, and then is extracted with diethyl ether twice. The ether extracts are washed with saturated sodium chloride solution, and with ice added the mixture is extracted with 2.36 ml. of concentrated hydrochloric acid in 25 ml. of water. The acid layer is then treated with 2.29 grams of potassium cyanate in 30 ml. of water at 20° C. After stirring for an hour, the mixture is heated to 0.5 hour and cooled. The product is collected by filtration, washed with water, and dried to give 2.75 grams, melting point 218.5° C. to 221.5° C.; $[\alpha]_{589}^{25}$ −63.2°, $[\alpha]_{436}$ −149.9°, $[\alpha]_{365}$ −271.5°, of (−)-4,5,6,7-tetrahydrobenzo[b]-thien-4-ylurea.

Similarly, the salt of (+)-4,5,6,7-tetrahydrobenzo[b]thiophen-4-amine and (S)-(−)-N-benzoyl glutamic acid is treated in the above manner to afford (+)-4,5,6,7-tetrahydrobenzo[b]thien-4-ylurea, melting point 218° C. to 220° C.; $[\alpha]_{589}^{25}$ +60°, $[\alpha]_{436}$ +149.8°, $[\alpha]_{365}$ +272.5°.

EXAMPLE 30

Preparation of 4,5,6,7-tetrahydrobenzo[b]thien-4-yl isocyanate

A sample of 47.6 grams of 4,5,6,7-tetrahydrobenzo[b]thiophen-4-amine hydrochloride is stirred in 150 ml. of water, and 350 ml. of 10% sodium hydroxide is added. The mixture is shaken and extracted with benzene twice. The extract is dried and evaporated to dryness to afford the amine, which is stored under nitrogen. The amine is then added dropwise to 866 ml. of 12.5% phosgene solution (benzene) in nitrogen atmosphere at 20° C. After stirring for an hour at room temperature, the mixture is gradually heated to 60° C. and kept at this temperature for 7 hours. The mixture is cooled to room temperature and evaporated to dryness to afford a residue, which is distilled to give 22.4 grams, boiling point 98° C. to 101° C./0.6 Torr., of 4,5,6,7-tetrahydrobenzo[b]thien-4yl isocyanate.

EXAMPLE 31

Preparation of 4,5,6,7-tetrahydrobenzo[b]thien-4-ylurea

A sample of 4,5,6,7-tetrahydrobenzo[b]thiophen-4-amine (19.9 grams) is cooled in a flask, and a solution of 12 ml. of 12N hydrochloric acid in 50 ml. of water is slowly added. Subsequently, at about 20° C., a solution of 11.7 grams of potassium cyanate in 80 ml. of water is added in 0.5 hour. The mixture is stirred at room temperature for one hour and then warmed to 60° C. and kept at this temperature for 0.5 hour. After standing overnight at room temperature, the product is collected and washed with water to afford 21 grams, melting point 206° C. to 209° C.

EXAMPLE 32

Mouse Growth Regulant Tests

CFI female mice from Carworth Farms are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreated controls are included in each test. Test data are provided in Tables VI, VII, VIII, and IX below wherein data are reported as percent weight gain over controls. Unless otherwise indicated in these tables, all compounds tested were dl-racemic mixtures. The following is a description of the diet to which the growth promoting compounds were added.

DIET

GUARANTEED ANALYSIS

| | |
|---|---|
| Crude protein not less than | 23.0 % |
| Crude fat not less than | 4.5 % |
| Crude fiber not more than | 6.0 % |
| Ash not more than | 9.0 % |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE VI

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_5$ | $R_6$ | $R_1$ | $R_3$ | $R_2$ | % Weight Gain over Controls |
|---|---|---|---|---|---|---|---|
| 50 | O | H | H | H | H | H | 50.1 |
| 400 | O | H | H | H | H | H | 119.6 |
| 50 | O | H | H | H | H | —$CH_3$ | 61.8 |
| 200 | O | H | H | H | H | H | 134.2 |
| 50 | O | H | H | H | H | —$C_2H_5$ | 40.3 |
| 200 | O | H | H | H | H | —$C_2H_5$ | 87.6 |
| 400 | O | H | H | H | —$CH_3$ | —OH | 49.6 |
| 400 | O | H | H | H | H | —$OCH_3$ | 68.6 |
| 400 | O | H | H | H | —$CH_3$ | —$CH_3$ | 55.1 |
| 400 | O | H | H | H | —$CH_3$ | —$OCH_3$ | 106.8 |
| 400 | O | H | H | H | H | —$CH(CH_3)_2$ | 88.0 |
| 400 | O | Br | H | H | H | H | 76.3 |
| 400 | O | Cl | H | H | H | H | 4.8 |
| 400 | O | H | H | —$CH_3$ | | H | 27.2 |
| 400 | S | —$CH_3$ | H | H | —$CH_3$ | H | 88.5 |
| 400 | O | H | H | H | H (levorotatory enantiomorph) | H | 122.5 |
| 400 | O | H | H | H | H | —$CH_3$ | 134 |
| 400 | O | H | H | H | H | —$C_2H_5$ | 87.6 |
| 400 | O | H | H | H | H | n-hexyl | 14.5 |
| 400 | O | H | H | H | H | —$CH_2C_6H_5$ | 32.4 |
| 400 | O | H | H | H | H | —$CH_2CH_2C_6H_5$ | 72.3 |
| 400 | S | H | H | H | H | —$C_2H_5$ | 54.6 |
| 400 | O | H | H | H | H | —$CH_2$—$CH_2$—O—$CH_2$—$CH_2$— | 9.9 |
| 400 | O | H | H | H | H | —$CH_2$—CH=$CH_2$ | 48.4 |
| 400 | O | H | H | H | H | 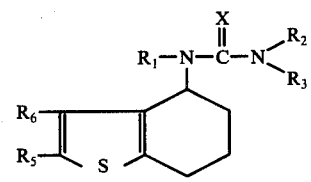 | 43 |
| 400 | O | H | H | H | H | —$CH_2$—$CH_2$—$CH_2$—$CH_2$— | 18 |
| 400 | O | H | H | H | -n-butyl | -n-butyl | 6 |
| 400 | S | H | H | H | H | H | 11 |
| 400 | S | H | H | H | H | —$CH_2$—$CH_2$—⟨N pyridyl⟩ | 15 |
| 400 | S | H | H | H | H | -n-butyl | 75 |
| 400 | O | H | H | H | H | —$CH_2$—$CH_2$—OH | 3 |
| 400 | S | H | H | H | H | -n-$C_8H_{17}$ | 16 |

TABLE VI-continued

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_5$ | $R_6$ | $R_1$ | $R_3$ | $R_2$ | % Weight Gain over Controls |
|---|---|---|---|---|---|---|---|
| 400 | S | H | H | H | H | cyclopropyl | 32 |
| 400 | S | H | H | H | H | $-CH_2-CH=CH$ | 60 |
| 400 | O | H | H | H | H | $-CH_2-C\equiv CH$ | 82 |
| 400 | O | H | H | H | H | 1-(1,2,3,4-tetrahydronaphthyl) | 4 |
| 400 | O | H | H | H | H | $-CN$ | 1 |
| 400 | O | H | H | H | H | (methyl-bromo-cyclohexyl) | 1 |
| 400 | O | H | H | H | H | indanyl | 8 |
| 200 | O | H | H | H | H | -n-butyl | 25 |
| 400 | O | H | H | H | H | $-CH_2-O-CH_3$ | 102 |
| 400 | O | H | H | H | H | $-CH_2CN$ | 12 |
| 400 | O | H | H | H |   | spiro piperidine structure with $-(CH_2)_2\diagdown C \diagup (CH_2)_2-$, $O=C$, HN, $N-C_6H_5$ | 14 |
| 400 | O | H | H | H | H | 2,4-dichlorophenyl | 18 |
| 400 | O | H | H | H | $-CH_3$ | $-CH_2C\equiv CH$ | 29 |
| 400 | O | H | H | H | H | $-NH-CO_2CH_3$ | 18 |
| 400 | O | H | H | H | H | $-CH_2-NH-CO-NH-$(4,5,6,7-tetrahydrobenzo[b]thienyl) | 29 |
| 400 | O | H | H | H | H | 4-methoxyphenyl | 78 |
| 400 | O | H | H | H | $-CH_2-CH=CH_2$ | $-CH_2-CH=CH_2$ | 4.0 |
| 400 | O | H | H | H | H | $-CH_2-$(thienyl) | 39 |
| 400 | O | H | H | H | $-CH_2-C\equiv CH$ | $-CH_2-C\equiv CH$ | 27 |

TABLE VI-continued
Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_5$ | $R_6$ | $R_1$ | $R_3$ | $R_2$ | % Weight Gain over Controls |
|---|---|---|---|---|---|---|---|
| 400 | O | H | H | H | H | —CH$_2$-(3-pyridyl) | 48 |
| 400 | O | H | H | H | H | —CH$_2$-(N-methylpyridinium iodide) | 6 |
| 400 | O | H | H | H | H | -(4-chlorophenyl) | 21 |
| 400 | O | H | H | H | H | —CH$_2$-(4-methoxyphenyl) | 16 |
| 400 | O | H | H | H | H | —CH$_2$-(2-pyridyl) | 41 |
| 400 | O | H | H | H | H | —CH$_2$-(4-pyridyl) | 46 |
| 400 | O | H | H | H | —(CH$_2$)$_2$—NH—(CH$_2$)$_2$— | | 3 |
| 400 | O | H | H | H | H | —CH$_2$CF$_3$ | 19 |
| 400 | O | H | H | H | H | —CH$_2$-(4-chlorophenyl) | 1 |
| 400 | O | H | H | H | | —(CH$_2$)$_3$-(2-methylphenyl) | 4 |
| 400 | O | H | H | H | —CH$_3$ | —CH$_2$C$_6$H$_5$ | 14 |
| 400 | O | H | H | H | H | —CH$_2$—CH(OCH$_3$)$_2$ | 22 |
| 400 | O | H | H | H | H | cyclopropyl | 31 |
| 400 | O | H | H | H | H | thiazolyl | 11 |
| 400 | O | H | H | H | —CH$_2$C$_6$H$_5$ | —CH$_2$—C≡CH | 30 |

TABLE VI-continued

Effectiveness of 4,5,6,7-Tetrahydrobenzo[b]thien-4-ylureas as
Animal Growth Promoting Agents Reported as Percent Weight
Gain Over Controls Using Mice as the Test Animal

| Rate ppm in Diet | X | $R_5$ | $R_6$ | $R_1$ | $R_3$ | $R_2$ | % Weight Gain over Controls |
|---|---|---|---|---|---|---|---|
| 400 | O | H | H | H | | $-(CH_2)_2-N-(CH_2)_2-$ with $p$-methoxyphenyl | 24 |
| 400 | O | H | H | H | | $-(CH_2)_2-$ and $-CH_2-$ forming ring with phenyl | 7 |
| 400 | O | H | H | H | H | $p$-nitrophenyl | 9 |
| 400 | O | H | H | H | H | 2,6-dimethylphenyl | 4 |
| 400 | O | H | H | H | H | $p$-ethoxyphenyl | 8 |
| 400 | O | H | H | H | H | $p$-n-butoxyphenyl | 9 |
| 400 | O | H | H | H | H | $-OH$ | 102.9 |
| 400 | O | H | H | H | H | $-OCH_2C_6H_5$ | 7.8 |
| 400 | S | H | H | H | $-CH_3$ | $-OCH_3$ | 66 |
| 400 | O | H | H | H | H | $-OC_2H_5$ | 61 |
| 400 | O | H | H | H | H | $-O-CH_2-CH=CH_2$ | 5 |
| 400 | O | H | H | H | cyclohexyl | $-OH$ | 19 |
| 400 | O | H | H | H | H | $-O-n-C_6H_{13}$ | 29 |
| 400 | O | H | H | H | $-CH(CH_3)_2$ | $-OH$ | 32 |
| 400 | O | H | H | H | $-CH_2C_6H_5$ | $-OH$ | 12 |
| 400 | O | $-CH_3$ | H | H | -2-butyl | H | 2 |
| 400 | O | H | $-CH_3$ | H | H | H | 26 |
| 400 | O | H | $-CH_3$ | H | H | -n-hexyl | 21 |
| 400 | O | $-CH_3$ | $-CH_3$ | H | -2-butyl | H | 3 |
| 400 | O | $-CH_3$ | $-CH_3$ | H | H | H | 0 |
| 400 | O | $-NO_2$ | H | H | H | H | 17 |
| 400 | O | H | H | H | H | $-\overset{O}{\underset{\|}{C}}-CH_3$ | −1.4 |
| 400 | S | H | H | H | H | $-CO_2C_2H_5$ | 22.3 |

TABLE VI-continued
Effectiveness of 4,5,6,7-Tetrahydrobenzo[b]thien-4-ylureas as Animal Growth Promoting Agents Reported as Percent Weight Gain Over Controls Using Mice as the Test Animal

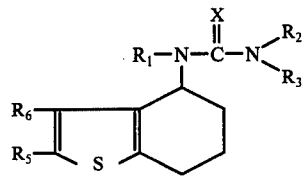

| Rate ppm in Diet | X | $R_5$ | $R_6$ | $R_1$ | $R_3$ | $R_2$ | % Weight Gain over Controls |
|---|---|---|---|---|---|---|---|
| 400 | O | H | H | H | H | 2,5-dimethoxyphenyl | 32.4 |
| 400 | O | H | H | H | H | 3-methoxyphenyl | 25.0 |
| 400 | O | H | H | H | H | $-N(CH_3)_2$ | 3.0 |
| 200 | O | H | H | H | H | $-C(=O)-CCl_3$ | 37.4 |
| 400 | S | H | H | H | H | 4-methoxyphenyl | −1.4 |
| 400 | O | H | H | H | H | $-O-$phenyl | 90.6 |
| 400 | O | H | H | H | H | $-OCH_2-CO_2H$ | 63.3 |
| 400 | 1-methyl-3-(4-methyl-4,5,6,7-tetrahydrobenzo[b]thien-4-yl)urea | | | | | | 39 |
| 400 | 1-methyl-3-(7,7-dimethyl-4,5,6,7-tetrahydrobenzo[b]thien-4-yl)urea | | | | | | 15 |

TABLE VII
Effectiveness of 4,5,6,7-Tetrahydrobenzo[b]thien-4-ylureas as Animal Growth Promoting Agents Reported as Percent Weight Gain Over Controls Using Mice as the Test Animal

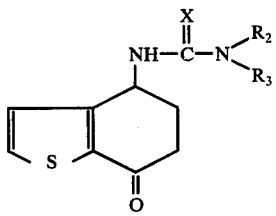

| Rate ppm in Diet | X | $R_3$ | $R_2$ | % Weight Gain Over Controls |
|---|---|---|---|---|
| 400 | O | H | $-CH_3$ | 64.8 |
| 400 | O | H | $-CH_2-CH=CH_2$ | 58.7 |
| 400 | O | H | $-C_2H_5$ | 79.3 |
| 200 | O | H | $-OCH_3$ | 71.0 |
| 200 | O | H | iso-$C_3H_7$ | 84.0 |
| 200 | O | $-CH_3$ | $-CH_3$ | 58.6 |
| 200 | O | H | $-CH_2-C\equiv CH$ | 40.6 |
| 200 | O | $-CH_3$ | $-OCH_3$ | 62.6 |
| 200 | O | $-CH_3$ | $-OH$ | 31.3 |

TABLE VII-continued
Effectiveness of 4,5,6,7-Tetrahydrobenzo[b]thien-4-ylureas as Animal Growth Promoting Agents Reported as Percent Weight Gain Over Controls Using Mice as the Test Animal

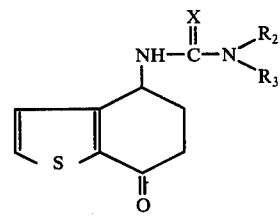

| Rate ppm in Diet | X | $R_3$ | $R_2$ | % Weight Gain Over Controls |
|---|---|---|---|---|
| 400 | O | H | $-C(=O)-CCl_3$ | 62.2 |
| 400 | S | H | $-CH_3$ | 62.5 |
| 200 | O | H | H | 9.4 |
| | | (dextrorotatory enantiomorph) | | |
| 25 | O | H | H | 118.6 |
| | | (levorotatory enantiomorph) | | |
| 400 | O | H | $-n-C_8H_{17}$ | 83.4 |
| 400 | 2-bromo-4,5,6,7-tetrahydro-7-oxo | | | 35.9 |

TABLE VII-continued

Effectiveness of 4,5,6,7-Tetrahydrobenzo[b]thien-4-ylureas as Animal Growth Promoting Agents Reported as Percent Weight Gain Over Controls Using Mice as the Test Animal

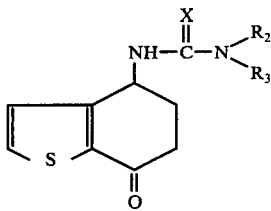

| Rate ppm in Diet | X | $R_3$ | $R_2$ | % Weight Gain Over Controls |
|---|---|---|---|---|
| | | benzo[b]thien-4-ylurea | | |
| 400 | O | H | -n-$C_{10}H_{21}$ | 15.4 |
| 400 | O | H | -n-$C_{12}H_{25}$ | 4.1 |
| 400 | O | H | -n-$C_{14}H_{29}$ | 9.7 |
| 400 | O | H | —$CH_2OCH_3$ | 142.8 |

TABLE IX

Effectiveness of 5,6,7,8-Tetrahydro-4H-cyclohepta[b]thien-4-ylureas as Animal Growth Promoting Agents Reported as Percent Weight Gain Over Controls Using Mice as the Test Animal

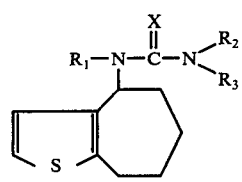

| Rate ppm in Diet | X | $R_1$ | $R_3$ | $R_2$ | % Weight Gain Over Controls |
|---|---|---|---|---|---|
| 400 | O | H | H | H | 54 |
| 400 | O | H | H | —$CH_3$ | 41 |
| 400 | S | H | H | —$C_2H_5$ | 40 |
| 400 | O | H | H | —$CH_2OCH_3$ | 10 |
| 400 | 5,6,7,8-tetrahydro-8-oxo-4H-cyclohepta[b]thien-4-ylurea | | | | 68.8 |

EXAMPLE 33

Preparation of 4,5,6,7-tetrahydrobenzo[b]thien-4-yl isothiocyanate

A sample (47.5 grams) of 4,5,6,7-tetrahydrobenzo[b]thiophen-4-amine hydrochloride is stirred in methylene chloride-water and 5% sodium hydroxide solution is added gradually until the pH is about 10. The methy-

TABLE VIII

Effectiveness of 4,5,6,7-Tetrahydrobenzo[b]thien-4-ylureas as Animal Growth Promoting Agents Reported as Percent Weight Gain Over Controls Using Mice as the Test Animal

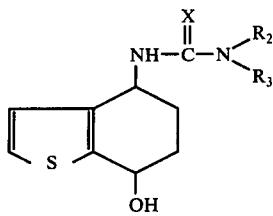

| Rate ppm in Diet | X | $R_3$ | $R_2$ | % Weight Gain Over Controls |
|---|---|---|---|---|
| 400 | O | H | —$CH_2$—CH=$CH_2$ | 29.1 |
| 200 | O | H | -iso-$C_3H_7$ | 43.9 |
| 400 | O | —$CH_3$ | —$CH_3$ | 81.5 |
| 400 | O | H | —$CH_3$ | 60.2 |
| 50 | O | H | —$CH_2$—C≡CH | 49.2 |
| 200 | O | —$CH_3$ | —$OCH_3$ | 60.5 |
| 200 | O | H | —$C_2H_5$ | 73.4 |
| 400 | S | H | —$CH_3$ | 85.1 |
| 400 | O | H | —$CH_2OCH_3$ | 123.7 |
| 400 | O | H | —$OCH_3$ | 66.7 |
| 50 | O | H | H | −11.3 |
| | | (dextrorotatory diastereomer, 95% isomer B) | | |
| 25 | O | H | H | 74.5 |
| | | (levorotatory diastereomer, 91.5% isomer B) | | |
| 25 | O | H | H | 54.4 |
| | | (levorotatory diastereomer, 86% isomer A) | | |
| 200 | O | H | H | 13.5 |
| | | (mixture of dextrorotatory diastereomers, 62% isomer B) | | |
| 25 | O | H | H | 3.7 |
| | | (dextrorotatory diastereomer, 90% isomer A) | | |

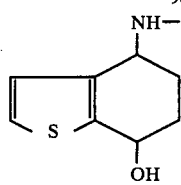

| | | | % Weight Gain Over Controls |
|---|---|---|---|
| 400 | | dl-cis (Isomer A) | 110 |
| 400 | | dl-trans (Isomer B) | 99 | lene chloride layer is removed and the aqueous layer is extracted with methylene chloride. The organic layers are combined, dried over magnesium sulfate, and evaporated to dryness to afford the oily amine. The amine is stirred in 500 ml. of ethyl acetate under nitrogen atmosphere and 25.4 grams of triethyamine is added. After about 15 minutes, 20.9 grams of carbon disulfide is added to afford a copius precipitate. An additional 200 ml. of ethyl acetate is added and the solid is pulverized with a spatula. After an hour of stirring, 51.5 grams of dicyclohexyl carbodiimide is added and stirring is continued for an overnight period. Subsequently, the mixture is heated at about 50° C. for 2 hours and cooled. The solid is removed by filtration and washed with ethyl acetate. The filtrate is evaporated to afford a mixture of solid and mostly oil. The solid is removed by filtration after either is added. The ether filtrate is evaporated to dryness to afford the crude isothiocyanate, which is purified by chromatography on a dry-column of silica gel using 65/35 (volume/volume) of petroleum ether/methylene chloride.

EXAMPLE 34

Preparation of N-(4,5,6,7-tetrahydrobenzo[b]thien-4-yl)-4-piperidine-thiocarboxamide In 50 ml. of tetrahydrofuran, 5.85 grams of 4,5,6,7-tetrahydrobenzo[b]thien-4-yl isothiocyanate is stirred and 2.81 grams of piperidine is added. An exotherm is observed and a temperature rises to about 40° C. to 50° C. After 2.5 hours, the mixture is heated at reflux temperature for 3.5 hours. After stirring overnight, the mixture is evaporated to dryness to afford a sticky yellow-brown solid. Ether is added to this material and the off-white, insoluble product is collected. The crude product, 5.25 grams, melts at 102° C. 104° C.

EXAMPLE 35

The following compounds set forth in Table X below were prepared by using the methods described in Example 3 and Example 5 and using the corresponding amines (diethyl ether solvent) or amine hydrochlorides (tetrahydrofuran solvent) with the appropriate isocyanates or isothiocyanates.

TABLE X

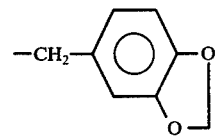

| $R_5$ | $R_6$ | $R_1$ | X | $R_3$ | $R_2$ | Reaction Solvent | Melting Point in degrees C. |
|---|---|---|---|---|---|---|---|
| H | H | —CH$_3$ | O | H | n-hexyl | ether* | 70.5–74.5 |
| H | H | —CH$_3$ | S | H | ethyl | ether | 104–107 |
| —CH$_3$ | H | H | S | H | ethyl | THF** | 118–121 |
| —CH$_3$ | H | H | O | H | ethyl | THF | 209–211 |
| —CH$_3$ | H | H | O | H | sec-butyl | THF | 182.5–185 |
| —CH$_3$ | H | H | O | H | n-hexyl | THF | 118–120 |
| H | —CH$_3$ | H | S | H | ethyl | THF | 120.5–123.5 |
| H | —CH$_3$ | H | O | H | sec-butyl | THF | 197–198 |
| H | —CH$_3$ | H | O | H | n-hexyl | THF | 148–150 |
| H | H | H | O | H | —CH$_2$CH=CH$_2$ | THF | 175–176 |
| H | H | H | O | H | —CH$_2$CO$_2$C$_2$H$_5$ | THF | 147–149 |
| H | H | H | S | H | $\begin{array}{c} O \\ \| \\ -C-C_6H_5 \end{array}$ | ether | 122–125 |
| H | H | H | O | H |  | ether | 219–221 |
| H | H | H | O | H | -n-C$_{12}$H$_{25}$ | ether | 109–111 |
| H | H | H | S | H | (cyclopentyl) | ether | 122–125 |
| H | H | H | O | H | 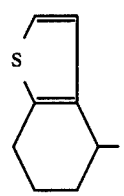 | ether | 279–283 |
| H | H | H | O | | —(CH$_2$)$_4$— | ether | 137–139 |
| H | H | H | O | | —(CH$_2$)$_5$— | ether | 128–130 |
| H | H | H | O | -n-C$_4$H$_9$ | -n-C$_4$H$_9$ | ether | 94–96 |

TABLE X-continued

Structure: R_1-N-C(=X)-N(R_2)(R_3) attached to a cyclohexene fused with a thiophene ring bearing R_5, R_6.

| R_5 | R_6 | R_1 | X | R_3 | R_2 | Reaction Solvent | Melting Point in degrees C. |
|---|---|---|---|---|---|---|---|
| H | H | H | S | H | —CH₂—CH₂—(2-pyridyl) | THF | oil |
| H | H | H | O | H | —CH₂CH₂—OH | ether | 140–154 |
| H | H | H | S | —(CH₂)₅— | | THF | 103–106 |
| H | H | H | S | H | -n-C₈H₁₇ | THF | 66–69 |
| H | H | H | S | H | cyclopropyl | THF | 125–129 |
| H | H | H | S | H | —CH₂CH=CH₂ | THF | 101–103 |
| H | H | H | S | H | —CH₂—(3,4-dimethoxyphenyl) | THF | 123–127 |
| H | H | H | S | H | —CH₂—(4-chlorophenyl) | THF | 137–144 |
| H | H | H | O | H | —CH₂—C≡CH | ether | 188–189 |
| H | H | H | O | H | 1-tetralinyl | THF | 287–292 |
| H | H | H | O | =C(S-CH₂-CH₂-S) (1,3-dithiolan-2-ylidene) | | ether | 126–128 |
| H | H | H | O | H | 2-thiazolin-2-yl | THF | 175–179 |
| H | H | H | O | H | —(4-methoxyphenyl) | CH₂Cl₂ | 223–226 |
| H | H | H | O | —CH₂—CH=CH₂ | —CH₂CH=CH₂ | ether | 69–72 |
| H | H | H | S | —CH₃ | —OCH₃ | CH₂Cl₂ | 74–77 |
| H | H | H | O | H | —OC₂H₅ | CH₂Cl₂ | 90–94 |
| H | H | H | O | H | —OCH₂—CH=CH₂ | CH₂Cl₂ | 70–73 |
| H | H | H | O | cyclohexyl | —OH | CH₂Cl₂ | 180–181 |
| H | H | H | O | H | —O-n-C₆H₁₃ | ether | 54–57 |
| H | H | H | O | —CH(CH₃)₂ | —OH | CH₂Cl₂ | 113–116 |
| H | H | H | O | —CH₂—CH=CH₂ | —CH₂—CH=CH₂ | ether | 69–72 |
| —CH₃ | H | H | O | H | H | H₂O | 234.5–236.5 |
| —CH₃ | H | H | O | H | -n-C₆H₁₃ | THF | 111–121 |
| H | —CH₃ | H | O | H | H | H₂O | 225–227 |
| —CH₃ | —CH₃ | H | S | H | —C₂H₅ | THF | 153–157 |
| —CH₃ | —CH₃ | H | O | H | -2-C₄H₉ | THF | 181–183.5 |
| —CH₃ | —CH₃ | H | O | H | —(4-chlorophenyl) | THF | 203–209 |
| —CH₃ | —CH₃ | H | O | H | H | H₂O | 233–237 |

TABLE X-continued

[Structure: R₁-N-C(=X)-N(R₂)(R₃) attached to cyclohexane fused with thiophene bearing R₅, R₆]

| R₅ | R₆ | R₁ | X | R₃ | R₂ | Reaction Solvent | Melting Point in degrees C. |
|---|---|---|---|---|---|---|---|
| H | H | H | O | H | —CN | H₂O | 142–145 |
| H | H | H | O | —(CH₂)₂—N(CO₂C₂H₅)—(CH₂)₂— | | ether | 110–113 |
| H | H | H | O | H | 2,5-dimethyl-4-bromophenyl | ether | 235–236 |
| H | H | H | O | H | 2-adamantyl | ether | 225–227 |
| H | H | H | O | H | indanyl | ether | 280–282 |
| H | H | H | O | H | —n-C₄H₉ | CH₂Cl₂ | 159–161 |
| H | H | H | O | H | —CH₂CN | THF | 179–181 |
| H | H | H | O | H | —CH₂—CH₂—OCH₃ | ether | 142–144 |
| H | H | H | O | —(CH₂)₂—C(=O)—(CH₂)₂— | | ether | 139–140 |
| H | H | H | O | H | —CH₂CH₂—S—CH₃ | ether | 128–130 |
| H | H | H | O | —(CH₂)₂—C(=O,HN—)(—(CH₂)₂—N—C₆H₅—) | | ether | 235–238 |
| H | H | H | O | H | —CH₂-(2-furyl) | ether | 183–185 |
| H | H | H | O | —CH₃ | —CH₂—C≡CH | ether | 105–108 |
| H | H | H | O | H | —CH₂—C(CH₃)=CH₂ | ether | 182–185 |
| H | H | H | O | H | —NH—CO₂CH₃ | ether | 183–186 |
| H | H | H | O | H | —CH₂—N(H)—CO—NH-(4,5,6,7-tetrahydrobenzothiophen-4-yl) | CH₃OH | 278–279 |
| H | H | H | O | H | —CH₂-(3-pyridyl) | CH₂Cl₂ | 171–172 |
| H | H | H | O | H | —CH₂-(N-methylpyridinium iodide) | CH₃OH | 184–187 |

TABLE X-continued

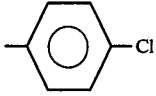

| $R_5$ | $R_6$ | $R_1$ | X | $R_3$ | $R_2$ | Reaction Solvent | Melting Point in degrees C. |
|---|---|---|---|---|---|---|---|
| H | H | H | O | H | -C₆H₄-Cl (4-chlorophenyl) | CH$_2$Cl$_2$ | 234–237 |
| H | H | H | O | H | -CH$_2$-(2-thienyl) | ether | 195–197 |
| H | H | H | O | -CH$_2$-C≡CH | -CH$_2$-C≡CH | ether | 118–120 |
| H | H | H | O | H | -CH$_2$-(4-pyridyl) | CH$_2$Cl$_2$ | 201–204 |
| H | H | H | O | H | -CH$_2$-(2-pyridyl) | CH$_2$Cl$_2$ | 192–195 |
| H | H | H | O | H | -CH$_2$-C$_6$H$_4$-OCH$_3$ | CH$_2$Cl$_2$ | 188–191 |
| H | H | H | O | H | -NH-CO-(2-furyl) | CH$_2$Cl$_2$ | 201–203 |
| H | H | H | O | H | -N(piperazinyl)N-C$_6$H$_5$ | CH$_2$Cl$_2$ | 141–144 |
| H | H | H | O | H | -CH$_2$CF$_3$ | CH$_2$Cl$_2$ | 208–211 |
| H | H | H | O | -CH$_3$ | -CH$_2$C$_6$H$_5$ | CH$_2$Cl$_2$ | 68–70 |
| H | H | H | O | H | -t-butyl | CH$_2$Cl$_2$ | 187–192 |
| H | H | H | O | H | -CH$_2$-C$_6$H$_4$-Cl | CH$_2$Cl$_2$ | 216–217 |
| H | H | H | O | H | -CH$_2$CH$_2$-N(CH$_3$)$_2$ | CH$_2$Cl$_2$ | 146–149 |
| H | H | H | O | H | -CH$_2$CH(OCH$_3$)$_2$ | CH$_2$Cl$_2$ | 125–128 |
| H | H | H | O | H | cyclopropyl | CH$_2$Cl$_2$ | 175–178 |
| H | H | H | O | H | 2-thiazolyl | THF | 207–210 |
| H | H | H | O | -CH$_2$C$_6$H$_5$ | -CH$_2$C≡CH | CH$_2$Cl$_2$ | 112–115 |
| H | H | H | O | -(CH$_2$)$_2$-N(-(CH$_2$)$_2$-)-C$_6$H$_4$-OCH$_3$ | | CH$_2$Cl$_2$ | 129–133 |

TABLE X-continued

[Structure: R_6 and R_5 on thiophene ring fused to cyclohexane; substituent R_1—N—C(=X)—N(R_2)(R_3) on the cyclohexane]

| $R_5$ | $R_6$ | $R_1$ | X | $R_3$ | $R_2$ | Reaction Solvent | Melting Point in degrees C. |
|---|---|---|---|---|---|---|---|
| H | H | H | O | H | 4-nitrophenyl | $CH_2Cl_2$ | 231–234 |
| H | H | H | O | H | 2,5-dimethylphenyl | $CH_2Cl_2$ | 241–242.5 |
| H | H | H | O | H | 2,4-dichlorophenyl | $CH_2Cl_2$ | 242–245 |
| H | H | H | O | H | 3,4-dimethoxyphenyl | $CH_2Cl_2$ | 200–204 |
| H | H | H | O | H | 4-$OC_2H_5$-phenyl | $CH_2Cl_2$ | 221–225 |
| H | H | H | O | H | 4-$OC_4H_9$-phenyl | $CH_2Cl_2$ | 183–186 |
| H | H | H | O | $-CH_2C_6H_5$ | —OH | $CH_2Cl_2$ | 121–123 |
| H | H | H | O | $-CH_2-$ (as part of tetrahydroisoquinoline: $-CH_2-C_6H_4-(CH_2)_2-$) | | $CH_2Cl_2$ | 143–146 |
| H | H | H | O | H | —O—$C_6H_{11}$ (cyclohexyloxy) | $CH_2Cl_2$ | 159–161 |
| H | H | H | O | $C_6H_5$ | —OH | $CH_2Cl_2$ | 131–133 |
| H | H | H | O | H | $-C(=O)-CH_3$ | THF | 173–176 |
| H | H | H | S | H | $-CO_2C_2H_5$ | THF | 146–148 |

TABLE X-continued $$R_1-N(H)-\underset{\underset{X}{\|}}{C}-N(R_2)(R_3)$$

(attached to tetrahydrobenzo[b]thiophene ring with $R_5$, $R_6$)

| $R_5$ | $R_6$ | $R_1$ | X | $R_3$ | $R_2$ | Reaction Solvent | Melting Point in degrees C. |
|---|---|---|---|---|---|---|---|
| H | H | H | O | H | 2,4-dimethoxyphenyl (–C₆H₃(OCH₃)₂) | $CH_2Cl_2$ | 206–207 |
| H | H | H | O | H | 3-methoxyphenyl (–C₆H₄OCH₃) | $CH_2Cl_2$ | 176–179 |
| H | H | H | O | H | —N(CH₃)₂ | ether* | 125–128 |
| H | H | H | O | H | —C(O)—CCl₃ | THF** | 149–151 |
| H | H | H | S | H | 4-methoxyphenyl (–C₆H₄OCH₃) | THF** | 149–150.5 |
| H | H | H | O | H | —O—C₆H₅ | ether* | 159–161 |
| H | H | H | O | H | —O—CH₂—CO₂H | $CH_2Cl_2$ | 142–145 |

*diethyl ether
**tetrahydrofuran

EXAMPLE 36

Preparation of 4,5,6,7-tetrahydro-2,3-dimethylbenzo[b]thiophen-4-amine hydrochloride 2,3-Dimethyl-6,7-dihydro-5H-benzo[b]thiophen-4-one is prepared in the manner described by Napier and Chu [International Journal of Sulfur Chemistry, A, 1, 62–64 (1971)]. This ketone is converted to 4-formylamino-4,5,6,7-tetrahydro-2,3-dimethylbenzo[b]thiophene by the method described by Kloetzel, Little, and Fish [Journal of Organic Chemistry, 18, 1511–1515 (1953)]. Hydrolysis of this formamido derivative is accomplished by using the method described in Example 19 to afford 4,5,6,7-tetrahydro-2,3-dimethylbenzo[b]thiophen-4-amine hydrochloride.

3-Methyl-6,7-dihydro-5H-benzo[b]thiophen-4-one is prepared similarly and converted to 3-methyl-4,5,6,7-tetrahydro benzo[b]thiophen-4-amine hydrochloride by the above sequence.

EXAMPLE 37

Preparation of 2-methyl-4,5,6,7-tetrahydrobenzo[b]thiophen-4-amine hydrochloride 2-Methylthiophene is converted to 2-methyl-6,7-dihydro-5H-benzo[b]thiophen-4-one by the method described by Fieser and Kennelly [Journal American Chemical Society, 57, 1611 (1925)]. This ketone is further converted to 2-methyl-4,5,6,7-tetrahydrobenzo[b]thiophen-4-amine hydrochloride by the methods cited in Example 36.

EXAMPLE 38

Preparation of 2-nitro-N-formyl-4,5,6,7-tetrahydrobenzo[b]-thien-4-ylurea

Acetic anhydride (30.8 ml.) is cooled to −10° C. to −12° C. and to the stirred solution is added dropwise 70% nitric acid (4 g. or 44.5 mmol). Over a period of 0.5 hour, N-formyl-4,5,6,7-tetrahydrobenzo[b]thiophen-4-amine (7.24 grams or 40 mmol) is added and the mixture is allowed to warm to room temperature over 2.5 hours and poured onto ice-water mixture (200 ml.). After stirring overnight, the sticky solid is filtered off and washed well with water. The air-dried, dark, sticky solid is triturated with ether (∼20 ml.), and the resulting nitro compound is filtered and washed with ether (10 ml.). The product, 2-nitro-N-formyl-4,5,6,7-tetrahydrobenzo[b]thiophen-4-amine, melts at 116° C. to 120° C. and weighs 3.25 grams.

Hydrolysis of the above formamide is accomplished by the method described in Example 19 to afford 2-nitro-4,5,67-tetrahydrobenzo[b]thiophen-4-amine hydrogen chloride, melting point > 260° C; infrared spectrum shows NO₂ bands at 1520 cm⁻¹ and 1335 cm⁻¹.

Conversion of the amine hydrogen chloride salt to 2-nitro-4,5,6,7-tetrahydrobenzo[b]thien-4-ylurea is accomplished by the method described in Example 10. It melts at 211° C. with decomposition after recrystallization from MeOH.

EXAMPLE 39

Preparation of 1-methyl-3-(5-iodo-4-methyl-4,5,6,7-tetrahydrobenzo[b]thien-4-yl)urea By the method of Kloetzel, Little, and Fish [Journal of Organic Chemistry, 18, 1511 (1953)], 4,5,6,7-tetrahydro-4-methylbenzo[b]thiophen-4-ol is prepared and dehydrated with fused sodium hydrogen sulfate by heating to afford 6,7-dihydro-4-methylbenzo[b]thiophen, boiling point 75°/0.9 Torr. This olefin (3 grams) is stirred with 3.9 grams of silver isocyanate in 50 ml. of dry ether under $N_2$ atmosphere at $-10°$ C. and 5.07 grams of iodine is added. After stirring for 1.25 hour at $-10°$ C. to 0° C. and then at 10° C. to 15° C. for 1.5 hours, the mixture is filtered over diatomaceous earth and the filter cake is washed with ether thoroughly. The filtrate is then treated with 2 ml. of 40% aqueous methyl amine to afford 1.62 grams, melting point 122° C. to 123° C., of 1-methyl-3-(5-iodo-4-methyl-4,5,6,7-tetrahydrobenzo[b]thien-4-yl)urea.

EXAMPLE 40

Preparation of 1-methyl-3-(4-methyl-4,5,6,7-tetrahydrobenzo[b]thien-4-yl)urea

Deiodination of 1-methyl-3-(5-idod-4-methyl-4,5,6,7-tetrahydrobenzo[b]thien-4-yl)urea is accomplished by treating a methanol mixture of this compound with palladium on carbon and magnesium oxide in a Paar hydrogenator at 50 psig. After uptake of the hydrogen is completed, the mixture is filtered through diatomaceous earth and filtrate is evaporated to dryness to afford 1-methyl-3-(4-methyl-4,5,6,7-tetrahydrobenzo[b]-thien-4-yl)urea, melting point 135° C. to 45° C.

EXAMPLE 41

Preparation of 7,7-dimethyl-4,5,6,7-tetrahydrobenzo[b]thien-4-ylurea

By the method described in Example 36 (first reference), 7,7-dimethyl-4,5,6,7-tetrahydrobenzo[b]thiophen-4-one is prepared and converted to 7,7-dimethyl-4,5,6,7-tetrahydrobenzo[b]thiophen-4-amine hydrochloride, melting point 211.5° C. to 215° C., by the remaining methods described in Example 36. The amine hydrochloride is converted to 7,7-dimethyl-4,5,6,7-tetrahydrobenzo[b]thien-4-ylurea, melting point 184° C. to 189° C. dec., by the method described in Example 10.

EXAMPLE 42

Preparation of 6,6-dimethyl-4,5,6,7-tetrahydrobenzo[b]thien-4-ylurea

By the method described in Example 36 (first reference), 6,6-dimethyl-4,5,6,7-tetrahydrobenzo[b]thiophen-4-one is prepared and converted to 6,6-dimethyl-4,5,6,7-tetrahydrobenzo[b]thiophen-4-amine hydrochloride (melting point > 300° C.) by the two remaining methods cited in Example 36. The amine hydrochloride is then converted to 6,6-dimethyl-4,5,6,7-tetrahydrobenzo[b]thien-4-ylurea, melting point 174° C. to 178° C., by the method outlined in Example 10.

EXAMPLE 43

Preparation of 1-methyl-3-(5-methyl-4,5,6,7-tetrahydrobenzo[b]thien-4-yl)urea

Diisopropylamine (7.3 grams or 72 mmol) is cooled and stirred in 60 ml. of dry tetrahydrofuran (THF) and 45 ml. (72 mmol) of 1.6N n-butyl lithium in hexane is added to $< -5°$ C. Five minutes later a solution of 4,5,6,7-tetrahydrobenzo[b]thiophen-4-one, 12 grams of 60 mmol in 30 ml. of THF is added dropwise at 0° C. to $-10°$ C. After stirring for 30 minutes at room temperature, 38 grams (270 mmol) of methyl iodide is added at <30° C. After stirring for 40 hours at room temperature, 100 ml. of water is added and the THF is removed in vacuo. The residue is extracted with 3×50 ml. of methylene chloride and the combined extracts are washed with 50 ml. of 2N hydrochloric acid, 50 ml. of 1M sodium carbonate, and 50 ml. of brine, respectively. The solution is dried (magnesium sulfate) and evaporated in vacuo to afford 9.46 grams of light brown oil. The oil is purified by chromatography on a silica-gel dry column using 1:1 hexane/methylene chloride to afford 6.9 grams of 5-metyl-4,5,6,7-tetrahydrobenzo[b]thiophen-4-one. This ketone is converted to 5-methyl-4,5,6,7-tetrahydrobenzo[b]thiophen-4-amine hydrochloride by the method cited in Example 36 and then the amine hydrochloride is converted to 1-methyl-3-(5-methyl-4,5,6,7-tetrahydrobenzo[b]thien-4-yl)urea, melting point 173° C. to 182° C., by the method described in Example 1.

Similarly, alkylation of 4,5,6,7-tetrahydrobenzo[b]thiophen-4-one with ethyl iodide, propyl iodide, and butyl iodide affords the corresponding 5-alkyl ketones, which are converted in the above manner to 1-methyl-3-(5-ethyl-4,5,6,7-tetrahydrobenzo[b]thien-4-yl)urea, 1-methyl-3-(5-propyl-4,5,6,7-tetrahydrobenzo[b]thien-4-yl)urea, and 1-methyl-3-(5-butyl-4,5,6,7-tetrahydrobenzo[b]thien-4-yl)yrea, respectively.

EXAMPLE 44

Preparation of 1-(methoxymethyl)-3-(4,5,6,7-tetrahydrobenzo[b]thien-4-yl)urea

In 150 ml. of methanol, 8.24 grams of 4,5,6,7-tetrahydrobenzo[b]thien-4-ylurea is stirred and 2.1 grams of sodium hydroxide pellets followed by 2.31 grams of paraformaldehyde in 50 ml. of methanol are added. The mixture is heated at reflux for 10 hours and cooled to afford crystals which are collected. The filtrate is evaporated to dryness and the residue is washed with water to afford 6.7 grams of solid. Recrystallization of the combined fractions from acetone-hexane gives 5.3 grams of 1-(methoxymethyl)-3-(4,5,6,7-tetrahydrobenzo[b]thien-4-yl)urea, melting point 160° C. to 162° C.

EXAMPLE 45

Preparation of 4,5,6,7-tetrahydrobenzo[b]thien-4-yl thiourea

A mixture of 13.21 grams o 1-benzoyl-3-(4,5,6,7-tetrahydrobenzo[b]thien-4-yl)thiourea in 100 ml. of 10% sodium hydroxide solution is heated to reflux for 10 minutes and cooled. The solid is collected and dissolved in 95% ethanol and the solution is evaporated to afford 9 grams of white solid. Recrystallization of this solid from chloroform/hexane affords 8.13 grams of 4,5,6,7- tetrahydrobenzo[b]thien-4-yl thiourea, melting point 129° C. to 131° C.

EXAMPLE 46

Preparation of 4,5,6,7-tetrahydrobenzo[b]thien-4-ylurea

A sample of 6 grams of 4,5,6,7-tetrahydrobenzo[b]thien-4-ylurea is dissolved in 375 ml. of 50% aqueous acetic acid and 75 grams of ceric ammonium nitrate is added in portions over a 10 minute period with stirring at 25° C. to 35° C. The pale-orange solution is stirred for another 5 minutes and 100 ml. of water is added. The solution is extracted twice with ethyl acette 450 ml. and 350 ml.) and the combined extracts are washed with 100 ml. of water. The organic extract is evaporated to dryness in vacuo and the brown residue is crystallized from methanol to afford 2.37 grams of 4,5,6,7-tetrahydro-7-oxobenzo[b]thien-4-ylurea, melting point 237° C. to 238° C. dec. Recrystallization from methanol affords purified product, melting point 245° C. to 246° C. dec.

Similarly, 1-methyl-3-(4,5,6,7-tetrahydro-7-oxobenzo[b]thien-4-yl)urea, 1-ethyl-3-(4,5,6,7-tetrahydro-7-oxobenzo[b]thien-4-yl)urea, 1-n-hexyl-3-(4,5,6,7-tetrahydro-7-oxobenzo[b]thien-4-yl)urea, 1-n-dodecyl-3-(4,5,6,7-tetrahydro-7-oxobenzo[b]thien-4-yl)urea, and 1-phenyl-3-(4,5,6,7-tetrahydro-7-oxobenzo[b]thien-4-ylurea, and the optical isomers of the 4,5,6,7-tetrahydro-7-oxobenzo[b]thien-4-ylureas are prepared by the above procedure starting with the corresponding ureas.

Substitution of the ceric ammonium nitrate with silver oxide, chromic anhydride or sodium dichromate also affords the above mentioned 7-oxo compounds. Chromic anhydride in acetic anhydride, followed by hydrolysis, also affords the 7-oxo compounds. The above-mentioned 7-oxo derivatives are also prepared by oxidizing their corresponding 7-hydroxycycloalkano[b]thien-4-ylurea in a similar manner.

EXAMPLE 47

Preparation of 1,1-dimethyl-3-(4,5,6,7-tetrahydro-7-oxobenzo[b]thien-4-yl)urea

A solution of 4,5,6,7-tetrahydro-7-oxobenzo[b]thiophen-4-amine (10.5 g.) in tetrahydrofuran (70 ml.) is added dropwise under nitrogen atomsphere to a solution of dimethylcarbamoyl chloride (6.72 g.) and triethylamine (12.6 g.) in tetrahydrofuran (70 ml.). After stirring for 20 hours, the mixture is evaporated to dryness and cold water (100 ml.) is added to the residue. The solid product is collected and air-dried. Recrystallization from acetone-hexane affords 3.7 g. of 1,1-dimethyl-3-(4,5,6,7-tetrahydro-7-oxobenzo[b]thien-4-yl)urea, m.p. 195° C. to 197° C.

Similarly, dibutylcarbamoyl chloride, dipropylcarbamoyl chloride and diethylcarbamoyl chloride are used in place of dimethylcarbamoyl chloride to afford 1,1-dibutyl-, 1,1-dipropyl-, and 1,1-diethyl-3-(4,5,6,7-tetrahydro-7-oxo-benzo[b]thien-4-yl)urea, respectively.

Substitution of the above-mentioned carbamoyl chlorides with the corresponding thiocarbamoyl chlorides affords the corresponding thioureas.

EXAMPLE 48

Preparation of 1,1-dimethyl-3-(4,5,6,7-tetrahydrobenzo[b]thien-4-yl)urea

Equimolar quantities of 4,5,6,7-tetrahydrobenzo[b]thien-4-amine, dimethylcarbomyl chloride and sodium hydroxide in water are stirred overnight. The crude product, 1,1-dimethyl-3-(4,5,6,7-tetrahydrobenzo[b]thien-4-yl)urea is collected and washed well with water. Recrystallization from acetone-hexane-ether affords pure product, m.p. 117° C. to 120° C.

Similarly, diethyl-, dipropyl-, and dibutylcarbamoyl chloride are reacted with 4,5,6,7-tetrahydrobenzo[b]thiophen-4-amine to afford 1,1-diethyl-, 1,1-dipropyl-, and 1,1-dibutyl-3-(4,5,6,7-tetrahydrobenzo[b]thien-4-yl)urea, respectively. Substitution of the above-mentioned carbamoyl chlorides with the corresponding thiocarbamoyl chlorides affords the corresponding thioureas.

EXAMPLE 49

Preparation of (+)— and (−)-4,5,6,7-tetrahydrobenzo[b]thiophen-4-amine

A mixture of 145.15 grams of (−)-4,5,6,7-tetrahydrobenzo[b]thiophen-4-ammonium (R)-N-benzoyl glutamate in 900 ml. of water and 50 grams of ice is stirred with 82 grams of NaOH in 1265 ml. of water. The mixture is extracted with 700 ml. and 500 ml. volumes of diethyl ether and the combined ether solutions are washed with brine and dried over $Na_2SO_4$. The ether solution is evaporated in vacuo to afford 52.85 grams of a colorless liquid; $[\alpha]_D^{24} = +57.12°$ ($c$, 4.16 in benzene) for the (+)-amine.

Similarly, (+)-4,5,6,7-tetrahydrobenzo[b]thiophen-4-ammonium (S)-N-benzoyl glutamate was treated with base to affod the (−)-amine, $[\alpha]_D^{25} = -56.35°$ ($c$, 3.05 in benzene).

EXAMPLE 50

Preparation of (−)- and (+)-N-(4,5,6,7-tetrahydrobenzo[b]thien-4-yl)formamide

In nitrogen atmosphere, 48.9 grams of 97% formic acid is added dropwise (over 15 minutes) to a stirred mixture of (+)-4,5,6,7-tetrahydrobenzo[b]thiophen-4-amine in 275 ml. of toluene at below 35° C. The mixture is heated at reflux using a Dean-Stark trap to remove water by azeotropic distillation. After 5.5 hours, very little water is distilled and thus the mixture is cooled. On cooling, the white product which crystallizes is collected. Additional product is obtained when the toluene filtrate is concentrated. The combined crops are washed with 500 ml. of water and then with 150 ml of cold hexane. The yield of the (−)-formamide is 60.5 grams, m.p. 132.5° -134° C., $[\alpha]_D^{24} = -119.67°$ ($c$, 4.18 in $CHCl_3$), $[\alpha]_D^{24} = -126.5°$ ($c$, 4.10 in HOAc).

Similarly, the (−)-4,5,6,7-tetrahydrobenzo[b]thiophen-4-amine is converted to (+)-N-(4,5,6,7-tetrahydrobenzo[b]thien-4-yl)formamide, m.p. 132°–135° C., $[\alpha]_D^{25} = +126.99°$ ($c$, 4.08 in HOAc).

EXAMPLE 51

Preparation of (−)-N-(4,5,6,7-tetrahydro-7-oxobenzo[b]thien-4-yl)formamide

Ceric ammonium nitrate (726.9 grams) is added portionwise to a stirred solution of 59.6 grams of (−)-N-(4,5,6,7-tetrahydrobenzo[b]thien-4-yl)formamide in 1712 ml. of 50% aqueous acetic acid. The addition is completed in half an hour and the temperature is kept at 25°-28° C. After 15 minutes of stirring, the mixture is saturated with NaCl and extracted with $CH_2Cl_2$ (2 ×

1200 ml., 600 ml.) and the combined extracts are washed with 600 ml. of brine and then with 250 ml. of water. The water is counter-extracted with 250 ml. of CH$_2$Cl$_2$ and the CH$_2$Cl$_2$ solution is added to the main CH$_2$Cl$_2$ solution. The CH$_2$Cl$_2$ solution is evaporated to dryness in vacuo and the residual dark, gummy residue is stirred with 500 ml. of dry diethyl ether for 1.5 hour and the large lumps of solid are pulverized. The title compound is then collected, washed with diethyl ether, and dried. This gives 48.65 g., m.p. 130°–136° C., $[\alpha]_D^{24} = 144.4°$ (c, 0.51 in HOAc).

EXAMPLE 53

Preparation of (+)-N-(4,5,6,7-tetrahydro-7-oxobenzo[b]thien-4-yl)formamide

The title compound is prepared in the same manner as the (−) enantiomer (Example 51) and the product melts at 129°–134° C.; $[\alpha]_D^{25.5} = +140.3°$ (c, 1.06 in HOAc).

EXAMPLE 53

Preparation of (+)-4,5,6,7-tetrahydro-7-oxobenzo[b]thiophen-4-amine hydrochloride A mixture of (+)-N-(4,5,6,7-tetrahydro-7-oxobenzo[b]thien-4-yl)formamide (52.65 grams) in 525 ml. of 95% ethanol and 525 ml. of 2N HCl is heated at reflux for 2 hours. The mixture is cooled, filtered through glass wool and the filtrate is evaporated to dryness. The dark solid is dissolved in 180 ml. of water and the insoluble material is collected by filtration. The filter cake is washed with 70 ml. of water and the combined solution containing the title compound is used in the next operation. A 3 ml. solution is evaporated to dryness and the residue is dissolved in 95% ethanol. The ethanol solution is decolorized with activated carbon and filtered. The filtrate is evaporated to dryness to afford 0.5 grams of the title compound, m.p. 212°–214° C. (dec.), $[\alpha]_D^{26} = +3.56°$ (c, 0.59 in methanol).

Similarly, the (−)-4,5,6,7-tetrahydro-7-oxobenzo[b]thiophen-4-amine hydrochloride is prepared and used directly in the next operation as a solution.

EXAMPLE 54

Preparation of (−)-4,5,6,7-tetrahydro-7-oxobenzo[b]thien-4-ylurea

The aqueous solution (280 ml.) of (+)-4,5,6,7-tetrahydro-7-oxobenzo[b]thiophen-4-amine hydrochloride from Example 53 is stirred while 40 grams of KOCN in 95 ml. of water is added dropwise. The mixture is warmed to 70° C. for 1.5 hour and cooled to 10° C. The light brown solid is collected and washed well with 700 ml. of water. The product is then stirred with 110 ml. of cold methanol, collected, and washed with 50 ml. of cold methanol to afford 48 grams of the title compound, m.p. 247°–249.5° C. (dec.), $[\alpha]_D^{24} = -97.16°$ (c, 0.14 in methanol).

EXAMPLE 55

Preparation of (+)-4,5,6,7-tetrahydro-7-oxobenzo[b]thien-4-ylurea

As described in the preparation of the (−) enantiomer, the title compound is prepared in 82% yield; m.p. 243°–246° C. (dec.); $[\alpha]_D^{25.5} = +84.66°$ (c, 0.19 in methanol).

EXAMPLE 56

Preparation of (−)-4,5,6,7-tetrahydro-7-hydroxybenzo[b]thien-4-ylurea, isomers A and B In 2.5 liters of ethanol, 34.85 grams of (−)-4,5,6,7-tetrahydro-7-oxobenzo[b]thien-4-ylurea is stirred and 9.8 grams of NaBH$_4$ is added. The mixture is stirred overnight at room temperature, 1400 ml. of water is added, and after stirring for 0.5 hour the ethanol is evaporated in vacuo. The mixture is cooled and 25–30 ml. of acetic acid is added until no more foaming occurs. The mixture is stirred for 0.75 hour, filtered to collect the first crop and this solid is washed with water and dried. This solid is recrystallized from acetone and then from acetone/methanol to give 6.75 g. of isomer B of the title compound, m.p. 211°–213° C. (dec.), $[\alpha]_D^{25.5} = -23.23°$ (c, 3.11 in methanol). This material contains 92% isomer B and 8% isomer A when assayed by high pressure liquid chromatography.

The original mother liquor is evaporated in vacuo, using ethanol to aid in removing water as an azeotrope. The residue is extracted twice with boiling acetone (1400 ml. portions) and the extracts are concentrated until crystals formed. A total of 13.1 g. which contains both isomers A and B is obtained. By preparative high pressure liquid chromatography on silica gel using a solvent mixture (volume/volume) of 1800 hexane/1000 CHCl$_3$/425 methanol at a flowrate of 40 ml./minute, 180 milligrams of 86% pure isomer A of the title compound is separated. This material melts at 162°–167° C. (dec.); $[\alpha]_D^{25.5} = -93.56°$ (c, 2.02 in methanol).

The terms isomer A and isomer B are used for the geometric isomers of the title compound as the assignment of the cis and trans configurations have not been determined unequivocally.

EXAMPLE 57

Preparation of (+)-4,5,6,7-tetrahydro-7-hydroxybenzo[b]thien-4-ylurea, isomers A and B In the same manner as described in reducing the (−)-4,5,6,7-tetrahydro-7-oxobenzo[b]thien-4-ylurea, (+)-4,5,6,7-tetrahydro-7-oxobenzo[b]thien-4-ylurea is reduced with NaBH$_4$ to afford isomer B of the title compound, m.p. 216°–217° C. (dec.), $[\alpha]_D^{25.5} = +18.51°$ (c, 2.11 in methanol). This isomer is 95% pure by high pressure liquid chromatography. Isomer A of the title compound is also purified by high pressure liquid chromatography as a 90–95% pure material, m.p. The cis and trans configurations for isomers A and B have not been determined unequivocally.

EXAMPLE 58

Preparation of (−)-4,5,6,7-tetrahydrobenzo[b]thiophen-4-amine hydrochloride

A sample of 1.02 grams of (dl)-4,5,6,7-tetrahydro-7-oxobenzo[b]thiophen-4-amine hydrochloride is treated with 0.8 grams of sodium hydroxide in 13 ml. of water and the free amine is extracted with chloroform several times (total volume 200 ml.). The chloroform extract is washed with brine, dried over Na$_2$SO$_4$ under nitrogen atmosphere, and the solution is evaporated to dryness to afford the liquid amine. The amine is dissolved in 5 ml. of methanol and a solution of 0.75 grams of (+)-tartaric acid in 10 ml. of methanol is added. The mixture is warmed slightly and allowed to cool to room temperature. The crystals are collected and fractionally crystallized from 85-90 ml. of 95% ethanol to afford 0.6 grams of salt. This salt is treated with 0.8 grams of NaOH in 13 ml. of water and the mixture is extracted several times with $CHCl_3$ (total volume 200 ml.) the combined extracts are washed with brine, dried over $Na_2SO_4$ under nitrogen and the solution is evaporated to dryness. The residual amine is dissolved in 10 ml. of acetone and treated with a saturated solution of HCl in isopropyl alcohol (1-2 ml.) until solid no longer forms. The solid title compound is collected and dried; melting point 219°-221° C. (dec.); $[\alpha]_D^{28} = -14.23°$ (c, 0.91 in methanol).

EXAMPLE 59

Preparation of and separation of 7-hydroxy-4,5,6,7-tetrahydrobenzo[b]thien-4-ylurea into the cis and trans isomers 7-Keto-4,5,6,7-tetrahydrobenzo[b]-thien-4-ylurea (0.5 grams, 2.38 mm) is suspended in ethanol (50 ml.) and to the stirred solution is added solid sodium borohydride (0.5 grams, 13.2 mm). After stirring overnight the mixture is treated cautiously with 5% aqueous acetic acid (20 ml.). After stirring 15 minutes the solvent is removed, the residue dissolved in a small volume of methanol and percolated through a 1½' × 1¾ silica gel dry column eluting with 20% methanolic methylene chloride. The resulting gum is crystallized from ethyl acetate/methanol to afford 66 mg. (13% Y) of the more polar (L.L.C) alcohol (B), melting point 194° C. to 197° C. The mother liquor material is separated into its two major components 7-hydroxy-4,5,6,7-tetrahydrobenzo[b]thien-4-ylurea by high pressure liquid chromatography on "Spherosil XOA 400" using the solvent system: hexane (1800 ml.)/methanol (425)/chloroform (1000) flow rate ~ 13 ml./min.). This procedure affords the less polar alcohol A (29 mgs. 6% yield) melting point, 162° C. to 169° C. (methanol/ethyl acetate), and the more polar alcohol B (50 mg., 10% yield), melting point 197° C. to 198° C.

The following compounds set forth in Table XI below were prepared by reducing an appropriately substituted 7-keto-4,5,6,7-tetrahydrobenzo[b]thien-4-ylurea with sodium borohydride in ethanol as described immediately hereinabove. Unless otherwise indicated in Table XI, the products were isolated as a mixture of the cis and trans isomers.

TABLE XI

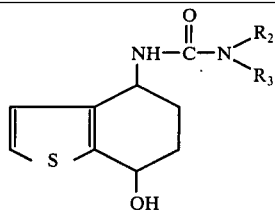

| $R_3$ | $R_2$ | Melting point in degrees C. |
|---|---|---|
| H | -n-$C_8H_{17}$ | 106-129 |
| H | —$CH_2$—CH=$CH_2$ | 173-176 |
| H | -iso-$C_3H_7$ | 180-187 |
| —$CH_3$ | —$CH_3$ | 218-225 |
| H | —$CH_3$ | 136-145 |
| H | —$CH_2$—C≡CH | 176-179 |
| —$CH_3$ | —$OCH_3$ | 179-182 |
| H | —$C_2H_5$ | 183-188 |
| H | —$OCH_3$ | 158-162 |

TABLE XI-continued

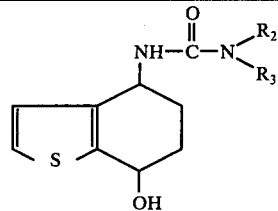

| $R_3$ | $R_2$ | Melting point in degrees C. |
|---|---|---|
| H | H | 190-195 |

(mixture of dextrorotatory diastereomers; 62 % isomer B)

EXAMPLE 60

Preparation of 2,4-bis[3'-methylureido]-4,5,6,7-tetrahydrobenzo[b]thiophene

2-Nitro-4-amino-4,5,6,7-tetrahydrobenzo[b]thiophene 2Nitro-4-amino-4,5,6,7-tetrahydrobenzo[b]thiophenehydrochloride (0.5 grams, 2.13 mmol) is dissolved in concentrated hydrochloric acid (4.3 ml.). The stirred solution is treated with stannous chloride dihydrate (2.56 grams, 11.35 mmol) added in portions over a 10 minute period (solution becomes hot). The brown solution is stirred for 3 hours, added to ice/water (20 ml.), made alkaline with 10% sodium hydroxide and the turbid solution extracted 3 times with methylene chloride (total volume ca. 100 ml.). The combined methylene chloride extracts are washed once with brine (20 ml.), dried (sodium sulfate) and evaporated to afford a gum. The gum is dissolved in methylene chloride (10 ml.) and ether (10 ml.) and the stirred solution treated with a solution of methyl isocyanate (0.5 grams, 8.8 mmol) in ether (10 ml.), added over a 10-minute period. The mixture is stirred overnight, then evaporated to dryness and the residue recrystallized from hot methanol to afford 230 mg. (38% yield) of 2,4-bis-[3'-methylureido]-4,5,6,7-tetrahydrobenzo[b]thiophene, melting point 233° C. to 234° C.

EXAMPLE 61

Preparation of N-formyl-4,5,6,7-tetrahydro-7-oxobenzo[b]thiophen-4-amine

In the manner described in Example 46, N-formyl-4,5,6,7-tetrahydrobenzo[b]thiophen-4-amine is oxidized with ceric ammonium nitrate to afford N-formyl-4,5,6,7-tetrahydro-7-oxobenzo[b]thiophen-4-amine, melting point 118° C. to 120° C. dec. This product is extracted from the reaction mixture with methylene chloride. The use of chromic anhydride in acetic anhydride followed by hydrolysis also affords the identical product.

Using the same work-up procedure, the following oxidants also afford the title compound which is isolated and/or analyzed for by spectroscopy (infrared and/or nuclear magnetic resonance). In Table XII below, the oxidant is expressed in terms of moles per mole of substrate.

TABLE XII

| Oxidant | Conditions | Yield |
|---|---|---|
| $K_2S_2O_8$ (2M)/$AgNO_3$ (catalytic) | In aqueous acetic acid at 50° C. | 27 % |

TABLE XII-continued

| Oxidant | Conditions | Yield |
|---|---|---|
| KMnO₄ (3.45M)/ Ce(NH₄)₂(NO₃)₆ (catalytic) | In aqueous acetic acid at less than 35° C. | 8 % |
| tert-butyl chromate (4.1M) | In CCl₄ at room temp. for four hours | 33 % |
| CrO₃ . 2 pyridine (11.9M) | In CH₂Cl₂ at room temp. overnight | 40 % |
| Ce(SO₄)₂ . 2H₂SO₄ (4M) | In aqueous acetic acid at room temp. | 60 % |
| H₂O₂/V₂O₅ (catalytic) (acetamide substrate instead of formamide) | In acetone at 34° C. overnight | 16 % |
| CrO₂Cl₂ (2M) (acetamide substrate instead of formamide) | In CH₂Cl₂ at less than 10° C. | 8.5 % |

EXAMPLE 62

Preparation of 4,5,6,7-tetrahydro-7-oxobenzo[b]thiophen-4-amine hydrochloride

In the manner described in Example 36, N-formyl-4,5,6,7-tetrahydro-7-oxobenzo[b]thiophen-4-amine is hydrolyzed with 2N hydrochloric acid/ethanol to afford 4,5,6,7-tetrahydro-7-oxobenzo[b]thiophen-4-amine hydrochloride, melting point 230° C. to 232° C. (dec.).

The free amine is obtained by neutralizing the amine hydrochloride in water with sodium hydroxide solution. It is separated by extraction with CHCl₃ and removal of the CHCl₃ in vacuo affords 4,5,6,7-tetrahydro-7-oxobenzo[b]thiophen-4-amine.

EXAMPLE 63

Preparation of 4,5,6,7-tetrahydro-7-oxobenzo[b]thien-4-yl isocyanate and urea

Conversion of 4,5,6,7-tetrahydro-7-oxobenzo[b]thiophen-4-amine hydrochloride to 4,5,6,7-tetrahydro-7-oxobenzo-[b]thien-4-yl isocyanate is accomplished by heating a toluene mixture of the hydrochloride at reflux temperature while phosgene is introduced. After the mixture becomes less cloudy, it is cooled and filtered. Evaporation of the filtrate affords the crude 4,5,6,7-tetrahydro-7-oxobenzo[b]thien-4-yl isocyanate; IR maximum = 2250 cm⁻¹.

Addition of NH₃/CH₃OH solution to this isocyanate affords 4,5,6,7-tetrahydro-7-oxobenzo[b]thien-4-ylurea.

EXAMPLE 64

The following compounds set forth in Table XIII below were prepared by allowing 4,5,6,7-tetrahydro-7-oxobenzo[b]-thiophen-4-amine hydrochloride to react with RNCX in the presence of an equimolar quantity of triethylamine in solvents such as aromatic solvents, chlorinated hydrocarbons, ethers, lower alkyl C₁–C₄ ketones, or mixtures thereof.

TABLE XIII

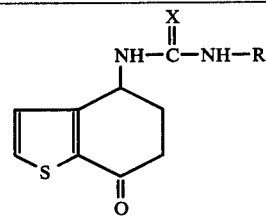

| | | Product | |
|---|---|---|---|
| RNCX | R | X | Melting Point in degrees C. |
| CH₃NCO | CH₃— | O | 212–215 |
| C₂H₅NCO | C₂H₅— | O | 188–190 |
| CCl₃C(=O)—NCO | Cl₃C—C(=O)— | O | 185–188 |
| C₆H₅CH₂NCO | C₆H₅CH₂— | O | |
| C₂H₅NCS | C₂H₅— | S | |
| CH₃O—CH₂NCO | CH₃—O—CH₂— | O | |
| CH₃O—CH₂NCS | CH₃—O—CH₂— | S | |
| CH₃O—C₆H₄—NCO | CH₃—C₆H₄— | O | |
| CH₃NCS | CH₃— | S | 161–164 |

EXAMPLE 65

The following compounds set forth in Table XIV below were prepared by reacting 4,5,6,7-tetrahydro-7-oxobenzo-[b]thien-4-yl isocyanate with the appropriate amines in inert solvents, as described before in Example 35.

TABLE XIV

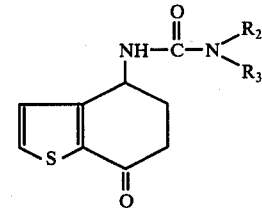

| | Product | |
|---|---|---|
| Amines | R₃ | R₂ |
| NH₂—OCH₃ | H | —OCH₃ |
| NH₂—OH | H | —OH |
| CH₃NH—OH | —CH₃ | —OH |
| CH₃NH—OCH₃ | —CH₃ | —OCH₃ |
| CH₂=CH—CH₂—NH₂ | H | —CH₂—CH=CH₂ |
| CH≡C—CH₂—NH₂ | H | —CH₂—C≡CH |
| (CH₃)₂NH | —CH₃ | —CH₃ |
| C₆H₅CH₂NH₂ | H | —CH₂—C₆H₅ |
| C₂H₅NH₂ | H | —C₂H₅ |
| n-C₄H₉NH₂ | H | -n-C₄H₉ |

TABLE XIV-continued $$\text{NH}-\overset{\overset{\text{O}}{\|}}{\text{C}}-\text{N}\overset{R_2}{\underset{R_3}{}}$$

(on 4,5,6,7-tetrahydrobenzo[b]thiophene with 7-oxo)

| Amines | Product R₃ | R₂ |
|---|---|---|
| CH₃C(O)—NH₂ | H | —C(O)—CH₃ |
| (pyridin-3-yl)CH₂—NH₂ | H | —CH₂—(pyridin-3-yl) |
| (furan-2-yl)CH₂—NH₂ | H | —CH₂—(furan-2-yl) |
| (CH₃)₂CH—NH₂ | H | —CH(CH₃)₂ |

EXAMPLE 66

By the method described in Example 59, the following compounds are prepared as cis and trans mixtures from their corresponding keto precursors:

Optically active isomers of 7-hydroxy-4,5,6,7-tetrahyrobenzo[b]thien-4-ylurea, 1-methyl-3-(7-hyroxy-4,5,6,7-tetrahydrobenzo[b]thien-4-yl)urea, 1-ethyl-3-(7-hydroxy-4,5,6,7-tetrahydrobenzo[b]thien-4-yl)urea, 1,1-dimethyl-3-(7-hydroxy-4,5,6,7-tetrahydrobenzo[b]thien-4-yl)urea, 1-methoxy-3-(7-hydroxy-4,5,6,7-tetrahydrobenzo[b]thien-4-yl)urea, 1-methyl-1-methoxy-3-(7-hydroxy-4,5,6,7-tetrahydrobenzo[b]-thien-4-yl)urea, 1-hydroxy-3-(7-hydroxy-4,5,6,7-tetrahydrobenzo[b]-thien-4-yl)urea, 1-hydroxy-1-methyl-3-(7-hydroxy-4,5,6,7-tetrahydrobenzo[b]thien-4-yl)urea, 1-methoxymethyl-3-(7-hydroxy-4,5,6,7-tetrahydrobenzo[b]thien-4-yl)urea, 1-allyl-3-(7-hydroxy-4,5,6,7-tetrahydrobenzo[b]thien-4-yl)-urea, and 1-(2-propynyl)-3-(7-hydroxy-4,5,6,7-tetrahydrobenzo[b]thien-4-yl)urea.

EXAMPLE 67

Preparation of 4,5,6,7-tetrahydrobenzo[b]thien-4-ylurea

A sample of 6,7-dihydrobenzo[b]thiophene is stirred in the cold in 96% sulfuric acid containing 4-6 mole equivalents of urea. After 1 hour the mixture is poured on ice and the organic phase is removed. Evaporation of the organic phase to dryness in vacuo affords 4,5,6,7-tetrahydrobenzo[b]-thien-4-ylurea.

EXAMPLE 68

Preparation of 4,5,6,7-tetrahydrobenzo[b]-thien-4-ylurea

A 1 gram sample of 4-hydroxy-4,5,6,7-tetrahydrobenzo[b]thiophene is stirred in the cold for several hours in thionyl chloride (5 ml.) and the mixture is evaporated to dryness. The crude 4-chloro-4,5,6,7-tetrahydrobenzo[b]thiophene is then added to a mixture of urea (1-5 mole-equivalents) in dimethylformamide and diisopropyl ethylamine. The mixture is warmed, after several hours, to 50° C. and after 4 hours is poured on ice and the product, 4,5,6,7-tetrahydrobenzo[b]thien-4-ylurea, is collected by filtration.

EXAMPLE 69

Preparation of 4,5,6,7-tetrahydrobenzo[b]thien-4-ylurea

A sample of 6,7-dihydrobenzo[b]thiophene is stirred with silver isocyanate and iodine as described in Example 39 and the resulting product, 5-iodo-4,5,6,7-tetrahydrobenzo[b]-thien-4-yl isocyanate is treated with concentrated ammonia solution to afford 5-iodo-4,5,6,7-tetrahydrobenzo[b]thien-4-ylurea. This latter product is then reduced in the manner described in Example 40 to afford 4,5,6,7-tetrahydrobenzo[b]-thien-4-ylurea.

The following products set forth in Table XV below were also obtained by reacting 5-iodo-4,5,6,7-tetrahydrobenzo[b]thien-4-yl isocyanate with R₂R₃NH to afford the corresponding iodo ureas, which were then hydrogenated in the above manner to give compounds of the formula:

TABLE XV $$\text{NH}-\text{CO}-\text{N}\overset{R_2}{\underset{R_3}{}}$$

(4,5,6,7-tetrahydrobenzo[b]thien-4-yl)

| R₃ | R₂ |
|---|---|
| H | —CH₃ |
| H | —C₂H₅ |
| H | —CH(CH₃)₂ |
| —CH₃ | —CH₃ |
| H | —OH |
| H | —OCH₃ |
| —CH₃ | —OH |
| —CH₃ | —OCH₃ |

When allyl amine and 2-propynyl amine are used to give 1-allyl- or 1-(2-propynyl)-3-(5-iodo-4,5,6,7-tetrahydrobenzo[b]thien-4-yl)urea, the resulting iodo ureas are deiodinated with tributyl tin hydride (Bu₃SnH). This reducing agent (Bu₃SnH) can also be used to deiodinate these aforementioned iodo ureas, while use of Zn/HCl gives the desired ureas and polymeric material.

EXAMPLE 70

Preparation of 1-(2-propynyl)-3-(4,5,6,7-tetrahydro-7-oxobenzo[b]thien-4-yl)urea.

A sample of 11.5 grams of 4,5,6,7-tetrahydro-7-oxobenzo[b]thiophen-4-amine is dissolved in 100 ml. of CH₂Cl₂ and the solution is added dropwise over 0.5 hours to 11 grams of carbonyl diimidazole stirred in 50 ml. of CH₂Cl₂. The mixture is stirred at room temperature for an hour and then added over a 0.5 hour period to 3.74 grams of 2-propargylamine in 50 ml. of CH₂Cl₂. After 3 hours, the crude title product is collected to afford 9.8 grams, m.p. 170°–183° C. Recrystallization from acetone-hexane gives 4.1 grams of title compound, m.p. 197°–199° C.

Similarly, when thiocarbonyl diimidazole is used instead of carbonyl diimidazole, the corresponding 1-(2-propynyl)-3-(4,5,6,7-tetrahydro-7-oxobenzo[b]-thien-4-yl)thiourea is obtained.

When the 1-(1-imidazolyl)-3-(4,5,6,7-tetrahydro-7-oxobenzo[b]thien-4-yl)urea is allowed to react with methyl methoxyamine, the product is 1-methoxy-1- methyl-3-(4,5,6,7-tetrahydro-7-oxobenzo[b]thien-4-yl)urea, m.p. 130°-136° C.

Other amines (R₂R₃NH) are used in the same manner to prepare the corresponding ureido compounds as listed in Table XVI below. Unless otherwise indicated in Table XVI, the products were isolated as the dl-racemates.

TABLE XVI

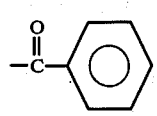

| R₃ | R₂ | Melting point in degrees C. |
|---|---|---|
| H | —CH₂—CH=CH₂ | 171-174 |
| H | —OCH₃ | 185-188.5 |
| H | -iso-C₃H₇ | 198-200 |
| —CH₃ | —CH₃ | 195-197 |
| —CH₃ | —OCH₃ | 126-129 |
| —CH₃ | —OH | 163-165.5 |
| H | -n-C₈H₁₇ | 105-108 |
| H | -C(O)-C₆H₅ | 204-207 |
| H | H (dextrorotatory enantiomorph) | 243-246 |
| H | H (levorotatory enantiomorph) | 247-249.5 |
| | 4,5,6,7-tetrahydro-2-bromo--7-oxobenzo[b]thien-4-ylurea | 252-253 |
| H | n-C₁₀H₂₁ | 104-107 |
| H | n-C₁₂H₂₅ | 83-86, 116-118 |
| H | n-C₁₄H₂₈ | 88-90, 114-116 |

EXAMPLE 71

Preparation of 1-methyl-3-(5,6,7,8-tetrahydro-4H-cyclohepta[b]thien-4-yl)urea 5,6,7,8-Tetrahydro-4H-cyclohepta[b]thiophen-4-one is converted to N-(5,6,7,8-tetrahydro-4H-cyclohepta[b]thien-4-yl)formamide, m.p. 164°-166° C., by the method of Kloetzel et al., Journal of Organic Chemistry 18, 1511 (1953). Hydrolysis of the formamide is accomplished by refluxing for one hour in 1N hydrochloric acid and evaporating to dryness to afford 5,6,7,8-tetrahydro-4H-cyclohepta[b]thiophen-4-amine hydrochloride, m.p. 233°-236° C. dec. The amine hydrochloride is then allowed to react with methyl isocyanate in dry tetrahydrofuran as solvent in the presence of a stoichiometric equivalent of triethylamine to afford 1-methyl-3-(5,6,7,8-tetrahydro-4H-cyclohepta[b]thien-4-yl)urea, m.p. 220°-222° C.

Similarly, by substituting ethyl isothiocyanate for methyl isocyanate in the above procedure there is obtained 1-ethyl-3-(5,6,7,8-tetrahydro-4H-cyclohepta[b]thien-4-yl)-2-thiourea, m.p. 117°-120° C.

EXAMPLE 72

Preparation of 5,6,7,8-tetrahydro-4H-cyclohepta[b]thien-4-ylurea

A mixture of 50 grams of 5,6,7,8-tetrahydro-4H-cyclohepta[b]thiophen-4-amine hydrochloride in 100 ml. of water is stirred at about 15° C. and a solution of 23.1 grams of potassium cyanate in 100 ml. of water is added dropwise. After completion of the addition, the mixture is warmed slowly to 70°-75° C. and held there for 1 hour. The mixture is cooled and the white solid is collected by filtration and washed with water. The solid is air-dried, pulverized, and washed with acetonitrile. Upon drying, this crude product is treated with hot acetone whereby there is obtained 5,6,7,8-tetrahydro-4H-cyclohepta[b]thien-4-ylurea, m.p. 217° C. dec.

EXAMPLE 73

Preparation of 1-(methoxymethyl)-3-(5,6,7,8-tetrahydro-4H-cyclohepta[b]thien-4-yl)urea In 150 ml. of methanol is stirred 8.24 grams of 5,6,7,8-tetrahydro-4H-cyclohepta[b]thien-4-ylurea and 2.1 grams of sodium hydroxide pellets followed by 2.31 grams of paraformaldehyde in 50 ml. of methanol. The mixture is heated at reflux for 10 hours and cooled to afford crystals which are collected. The filtrate is evaporated to dryness and the residue is washed with water to afford more solid. Recrystallization of the combined fractions from acetone-hexane gives 1-(methoxymethyl)-3-(5,6,7,8-tetrahydro-4H-cyclohepta[b]-thien-4-yl)urea, m.p. 197°-201° C. dec.

EXAMPLE 74

Preparation of 5,6,7,8-tetrahydro-4H-8-oxocyclohepta[b]thien-4-ylurea

In 375 ml. of 50% aqueous acetic acid is dissolved 6 grams of 5,6,7,8-tetrahydro-4H-cyclohepta[b]thien-4-ylurea, and 75 grams of ceric ammonium nitrate is added portionwise over a 10 minute period with stirring at 25°-35° C. The pale orange solution is stirred for another five minutes and 100 ml. of water is added. The solution is extracted twice with ethyl acetate (450 ml. and 350 ml.) and the combined extracts are washed with 100 ml. of water. The organic extract is evaporated to dryness in vacuo and the brown residue is recrystallized from methanol to afford 5,6,7,8-tetrahyro-4H-8-oxocyclohepta[b]thien-4-ylurea, m.p. 246°-248° C. dec.

EXAMPLE 75

Growth Enhancement and Feed Efficiency Evaluations in Sheep Given an Implant Containing Test Compound To determine the effect of a 4,5,6,7-tetrahydrobenzo[b]thien-4-ylurea compound on sheep, Wether lambs are randomly allotted to pens in groups of six. The sheep are weighed and permitted food and water ad libitum. The feed is weighed daily, and uneaten feed from the previous day is collected and weighed. Test lambs receive the same unmedicated diet as control animals, but test animals receive one or more subcutaneous implants containing test compound at the base of the ear. The formulation of the implant used is given below. At the end of the six-week treatment period, the lambs are again weighed, and total feed consumed is calculated.

In these tests, six replicates of six lambs each per treatment are used and each animal receives from about 11 mg. to 105 mg. of test compound.

Average six-week weight gains are presented in Table XVII and feed per pound of gain is presented in Table XVIII. From these data it can be seen that lambs implanted with 11 mg. or 99 mg. of test compound showed approximately a 10% increase in weight gain over untreated controls six-weeks after implantation. Feed utilization for the same period was also improved by about 5% over untreated controls.

LAMB DIET

|  | % |
|---|---|
| Ground Corn Cob | 15.0 |
| Ground Yellow Corn | 48.0 |
| Soybean Oil Meal (49%) | 10.0 |
| Dehydrated Alfalfa Meal | 15.0 |
| Molasses | 10.0 |
| Iodized Salt | 0.5 |
| Dicalcium Phosphate | 1.0 |
| Premix | 0.5 |
|  | 100.0 |

PREMIX FOR ONE TON

| Tra-Min No. 3[(1)] | 454 grams |
|---|---|
| Vitamin A (30,000 µ/g) | 133 grams |
| Vitamin D$_3$ (200,000 µ/g) | 5 grams |
| Corn Oil | 100 grams |
| Ground Corn | 3848 grams |
|  | 4540 |

| [(1)]Tra-min No. 3: | Calcium | 21.00% |
|---|---|---|
|  | Manganese | 12.50% |
|  | Iron | 6.00% |
|  | Zinc | 5.00% |
|  | Copper | 0.65% |
|  | Iodine | 0.35% |
|  | Cobalt | 0.25% |

Pellet Implant

| 4,5,6,7-Tetrahydrobenzo[b]thien-4-ylurea | 11.0 mg. |
|---|---|
| Glyceryl 12-hydroxystearate | 10.50 mg. |
| Magnesium stearate | 0.50 mg. |
|  | 22.00 mg. |

TABLE XVII

| | | Average 6-Week Weight Gain (kg.)/Lamb | | | | | | |
|---|---|---|---|---|---|---|---|---|
| | Drug | Replication | | | | | | |
| Treatment | Implants a/ | 1 | 2 | 3 | 4 | 5 | 6 | AV. |
| Control | 0 | 8.50 | 8.70 | 9.93 | 6.50 | 7.03 | 6.75 | 7.90 |
| 4,5,6,7-tetra-hydrobenzo[b]-thien-4-ylurea | 1 | 11.25 | 9.32 | 9.20 | 8.63 | 8.05 | 6.68 | 8.86 |
|  | 9 | 10.83 | 9.60 | 8.75 | 7.20 | 8.53 | 7.20 | 8.69 | a/ Approximate weight: 22 mg. each  Composition: 50% drug + 50% carrier

TABLE XVIII

| | | Average 6-Week Feed/Gain per Pen | | | | | | |
|---|---|---|---|---|---|---|---|---|
| | Number of Drug | Replication | | | | | | |
| Treatment | Implants a/ | 1 | 2 | 3 | 4 | 5 | 6 | AV. |
| Control | 0 | 7.88 | 6.77 | 7.41 | 8.82 | 9.18 | 8.16 | 8.04 |
| 4,5,6,7-tetra-hydrobenzo[b]-thien-4-ylurea | 1 | 6.63 | 6.58 | 7.41 | 8.21 | 8.05 | 8.49 | 7.57 |
|  | 9 | 6.51 | 6.75 | 7.80 | 8.38 | 7.56 | 7.97 | 7.49 | a/ Approximate weight: 22 mg. each  Composition: 50% drug + 50% carrier

EXAMPLE 76

Growth Enhancement and Feed Efficiency Improvement in Sheep Fed Levels of Test Compounds To determine the effect of feeding experimental compounds on sheep performance, Wether lambs are randomly allotted to pens in groups of six. The sheep are weighed and permitted feed and water ad libitum. The feed is weighed daily, and uneaten feed from the previous day is collected and weighed. Test lambs receive the same diet as control animals but with the addition of experimental compound at a concentration of either 15 or 60 ppm. At the end of the six-week treatment period, the lambs are again weighed, and total feed is calculated.

In these tests, five replicates of six lambs each per treatment are used. Experimental compounds are as follows:

A - 4,5,6,7-tetrahydrobenzo[b]thien-4-ylurea
B - 4,5,6,7-tetrahydro-7-oxobenzo[b]thien-4-ylurea Average daily gains for the six-week period are presented in Table XIX and feed per unit of gain is presented in Table XX. From these data it can be seen that lambs fed either 15 or 60 ppm of the test compounds showed improvements in weight gain and feed efficiency over untreated controls.

TABLE XIX

| | | Average Daily Gain (kg)/Lamb | | | | | |
|---|---|---|---|---|---|---|---|
| | Level | Replication | | | | | |
| Treatment | (ppm) | 1 | 2 | 3 | 4 | 5 | av. |
| Control | — | 0.175 | 0.223 | 0.169 | 0.159 | 0.185 | 0.182 |
| Compound A | 15 | 0.190 | 0.187 | 0.186 | 0.174 | 0.195 | 0.186 |
| Compound A | 60 | 0.211 | 0.250 | 0.200 | 0.193 | 0.189 | 0.208 |
| Compound B | 15 | 0.187 | 0.208 | 0.218 | 0.186 | 0.210 | 0.202 |
| Compound B | 60 | 0.216 | 0.207 | 0.237 | 0.189 | 0.190 | 0.208 |

TABLE XX

| | | Six-Week Feed/Gain | | | | | |
|---|---|---|---|---|---|---|---|
| | Level | Replication | | | | | |
| Treatment | (ppm) | 1 | 2 | 3 | 4 | 5 | av. |
| Control | — | 7.111 | 5.563 | 6.692 | 7.414 | 6.392 | 6.635 |
| Compound A | 15 | 6.777 | 6.174 | 6.158 | 7.626 | 6.319 | 6.611 |
| Compound A | 60 | 6.250 | 5.539 | 6.040 | 6.507 | 6.403 | 6.148 |
| Compound B | 15 | 6.785 | 6.067 | 5.344 | 6.795 | 6.089 | 6.216 |
| Compound B | 60 | 6.116 | 6.263 | 5.144 | 6.723 | 6.506 | 5.151 |

EXAMPLE 77

The following tests were conducted to evaluate the ability of 4,5,6,7-tetrahydrobenzo[b]thien-4-ylurea to promote growth in chicks.

In these tests day-old chicks are placed in heated cages and given feed and water ad libitum. In each test there are 5 male and 5 female chicks per cage and three cages per treatment are used. Treatments consist of a basal diet plus 1,3 or 9 ppm. of test compound. The chicks are weighed at the beginning and end of the experiment. Feed consumption is determined for the experimental period which is 13 days beginning when the chicks are one day old. The basal diet employed and results obtained are reported below.

| Chick Basal Diet | |
|---|---|
| Ground yellow corn | 53.45% |
| Soybean oil meal (49%) | 28.0 |
| Menhaden fish meal (60%) | 5.0 |
| Corn gluten meal (60%) | 5.0 |
| Dehydrated alfalfa meal (17%) | 2.0 |
| Stabilized fat | 4.0 |
| Dicalcium phosphate | 1.2 |
| Ground limestone | 0.5 |
| Sodium chloride | 0.3 |
| *Tra-Min No. 3 | 0.05 |
| **Vitamin premix | 0.5 |
| | 100.00 |

| **VITAMIN PREMIX FOR 1-TON | | |
|---|---|---|
| DL methionine | 453.6 | grams |
| BHT | 113.6 | |
| Vitamin A (30,000 μ/g) | 100.0 | |
| Vitamin $D_3$ (200,000 μ/g) | 5.0 | |
| Vitamin E (20,000 μ/lb.) | 45.4 | |
| Riboflavin | 4.0 | |
| Niacinamide | 25.0 | |
| Ca. Pantothenate | 8.0 | |
| Vitamin K (menadione) | 1.0 | |
| Parvo (10%), folic acid | 13.0 | |
| Choline chloride (50%) | 908.0 | |
| Proferm (20 mg/lb.), $B_{12}$ | 227.0 | |
| Corn oil | 50.0 | |
| Fine ground corn | 2582.4 | |
| | 4536.0 | |

| *Tra-Min No. 3 | | 1 lb/Ton Furnishes |
|---|---|---|
| Manganese | 12.50% | 62.5 ppm |
| Iron | 6.00% | 30.0 |
| Zinc | 5.00 | 25.0 |
| Copper | 0.65% | 3.25 |
| Iodine | 0.35% | 1.75 |
| Cobalt | 0.25% | 1.25 |
| Calcium | 15.30% Min. | |
| | 18.35% Max. | |

| | | Chick Tests | | | | | |
|---|---|---|---|---|---|---|---|
| | | Average 13-day Chick/Gain (g) | | | | | |
| | Level | Experiment | | | | | Percent |
| | (ppm) | 1928 | 1929 | 1930 | 1931 | AV. | Improvement |
| 1. Control | — | 189 | 175 | 180 | 188 | 183 | — |
| 2. 4,5,6,7- | 1 | 181 | 193 | 182 | 200 | 189 | 3.3 |
| tetrahydro- | | | | | | | |
| 3. benzo[b]- | 3 | 199 | 186 | 197 | 198 | 195 | 6.6 |
| thien-4- | | | | | | | |
| 4. ylurea | 9 | 190 | 198 | 191 | 191 | 193 | 5.5 |

| | | Average 13-day Feed/Gain | | | | | |
|---|---|---|---|---|---|---|---|
| | Level | Experiment | | | | | Percent |
| Treatment | (ppm) | 1928 | 1929 | 1930 | 1931 | AV. | Improvement |
| 1. Control | — | 1.54 | 1.52 | 1.46 | 1.48 | 1.50 | — |
| 2. 4,5,6,7- | 1 | 1.48 | 1.45 | 1.49 | 1.44 | 1.46 | 2.7 |
| tetrahydro- | | | | | | | |
| 3. benzo[b]- | 3 | 1.47 | 1.40 | 1.44 | 1.40 | 1.43 | 4.7 |
| thien-4- | | | | | | | |
| 4. ylurea | 9 | 1.45 | 1.45 | 1.46 | 1.40 | 1.44 | 4.0 |

EXAMPLE 78

Preparation of 1-(methoxymethyl)-3-(4,5,6,7-tetrahydro-7-hydroxybenzo[b]thien-4-yl)urea A mixture of 4,5,6,7-tetrahydro-7-hydroxybenzo[b]thien-4-yl urea (4 g., 18.87 mmole), sodium hydroxide (0.969 g., 24.22 mmole), paraformaldehyde (1.038 g., 34.6 mmole) and methanol (94 ml.) is stirred and heated at reflux under a nitrogen atmosphere for 23 hours. The mixture is allowed to cool and excess solid carbon dioxide is added. Evaporation in vacuo affords a solid which is stirred with water (50 ml.) for 2 hours, filtered and air dried to furnish 3.16 g., of the title compound (65% yield) m.p. 157°–159° C. dec. Recrystallization from hot acetone gives the analytical specimen 160°–161° C. dec.

EXAMPLE 79

Preparation of 1-(methoxymethyl)-3-(4,5,6,7-tetrahydro-7-oxobenzo[b]thien-4-yl)urea A solution of 1-(methoxymethyl)-3-(4,5,6,7-tetrahydro-7-hydroxybenzo[b]thien-4-yl)urea (0.35 g., 1.37 mmole) in acetone (40 ml.) is treated with manganese dioxide (3.5 g.). After 2 hours stirring the reaction mixture is filtered through celite, the cake washed thoroughly with acetone and the filtrate and washings evaporated to furnish 0.32 g. on 90.7% yield of the title compound as a crystalline solid, m.p. 155°–158° C. Recrystallization from hot acetone affords the analytical sample, m.p. 159°–162° C.

I claim:

1. A method for improving the feed efficiency and enhancing the growth rate of veterinary homothermic animals which comprises administering to said animals an effective amount of a compound selected from the group consisting of those of the formulae:

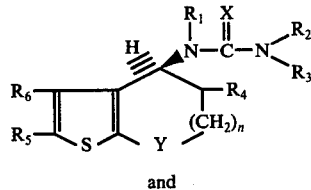

and

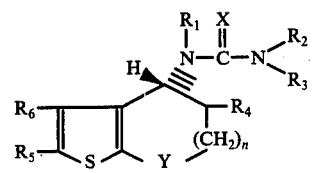

wherein X is oxygen or sulfur; n is the integer 1 or 2; Y is a divalent radical selected from the group consisting of those of the formulae:

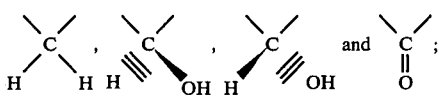

$R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and β-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

hydrogen
alkyl $C_1$-$C_8$
cycloalkyl $C_3$-$C_6$
allyl
2-propynyl
hydroxy
alkoxy $C_1$-$C_6$
allyloxy
methoxymethyl
phenoxy
—$CH_2$—$CH(OR)_2$
—$CH_2$—$CF_3$
—$CH_2$—$CN$
—$NH$—$CO_2R$
—$O$—$CH_2$—$CO_2H$
—$CO_2C_2H_5$

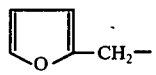

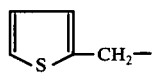

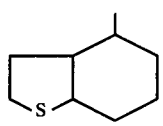

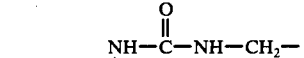

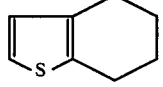

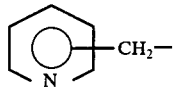

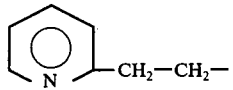

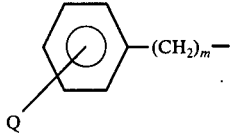

wherein R is alkyl $C_1$-$C_4$, m is 0, 1 or 2, and Q is selected from the group consisting of the substituents listed in the following table:

| m = 0 | m = 1 | m = 2 |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and $R_2$ and $R_3$ taken together with the associated N(itrogen) is selected from the group consisting of morpholino, piperidino, pyrrolidino, 4-(4-methoxyphenyl)-piperazino, 1,2,3,4-tetrahydroquniolino and the moiety of the formula:

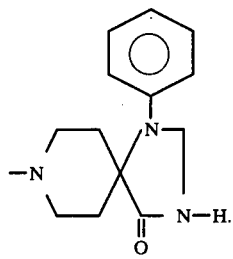

2. A method according to claim 1 wherein said compound is orally administered to said animals in an amount equivalent to between 0.0001% and 0.08% by weight of the animal feed.

3. A method according to claim 1 wherein said compound is parenterally administered as one or more subcutaneous implants beneath the skin of said animal and said implants being sufficient to provide a daily drug release of from 0.0005% mg. to 0.2 mg. of said compound per kg. of animal body weight.

wherein R is alkyl $C_1$-$C_4$, m is 0, 1 or 2, and Q is selected from the group consisting of the substituents listed in the following table:

| m = 0 | m = 1 | m = 2 |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and $R_2$ and $R_3$ taken together with the associated N(itrogen) is selected from the group consisting of morpholino, piperidino, pyrrolidino, 4-(4-methoxyphenyl)-piperazino, 1,2,3,4-tetrahydroquinolino and the moiety of the formula:

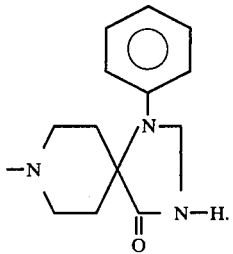

4. A method for improving the feed efficiency and enhancing the growth rate of veterinary homothermic animals which comprise administering to said animals an effective amount of a compound selected from the group consisting of the dextrorotatory enantiomorph, the levorotatory enantiomorph, and the racemic mixture thereof of a compound of the formula:

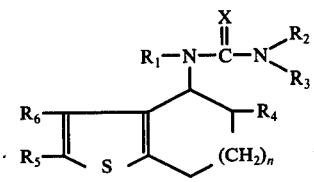

wherein X is oxygen or sulfur; $n$ is the integer 1 or 2; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and $\beta$-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

| |
|---|
| hydrogen |
| alkyl $C_1$-$C_8$ |
| cycloalkyl $C_3$-$C_6$ |
| allyl |
| 2-propynyl |
| hydroxy |
| alkoxy $C_1$-$C_6$ |
| allyloxy |
| methoxymethyl |
| phenoxy |
| —CH$_2$—CH(OR)$_2$ |
| —CH$_2$—CF$_3$ |
| —CH$_2$—CN |
| —NH—CO$_2$R |
| —O—CH$_2$—CO$_2$H |
| —CO$_2$C$_2$H$_5$ |
| ![furan-CH2] |
| ![thiophene-CH2] |
| ![cyclohexyl-thiophene] |
| NH—C(=O)—NH—CH$_2$— with tetrahydrobenzothiophene |
| ![pyridine-CH2] |
| ![pyridine-CH2CH2] |
| ![phenyl-(CH2)m-Q] | wherein R is alkyl $C_1$-$C_4$, $m$ is 0, 1 or 2, and Q is selected from the group consisting of the substituents listed in the following table:

| $m = 0$ | $m = 1$ | $m = 2$ |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and $R_2$ and $R_3$ taken together with the associated N(itrogen) is selected from the group consisting of morpholino, piperidino, pyrrolidino, 4-(4-methoxyphenyl)-piperazino, 1,2,3,4-tetrahydroquinolino and the moiety of the formula:

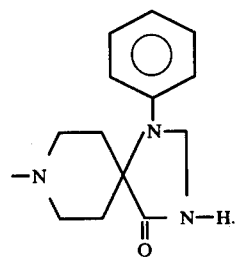

5. The method according to claim 4 wherein the compound is the racemic mixture wherein X is oxygen, $n$ is 1, and $R_1$, $R_2$, $R_3$, $R_4$, $R_5$ and $R_6$ are hydrogen; dl-4,5,6,7-tetrahydrobenzo[b]thien-4-ylurea.

6. The method according to claim 4 wherein the compound is the dextrorotatory enantiomorph wherein X is oxygen, $n$ is 1, and $R_1$, $R_2$, $R_3$, $R_4$, $R_5$ and $R_6$ are hydrogen; d-4,5,6,7-tetrahydrobenzo[b]thien-4-ylurea.

7. The method according to claim 4 wherein the compound is the levorotatory enantiomorph wherein X is oxygen, $n$ is 1, and $R_1$, $R_2$, $R_3$, $R_4$, $R_5$ and $R_6$ are hydrogen, l-4,5,6,7-tetrahydrobenzo[b]thien-4-ylurea.

8. The method according to claim 4 wherein the compound is the racemic mixture wherein X is oxygen, $n$ is 1, $R_1$ and $R_2$ are hydrogen, $R_3$ is methyl, and $R_4$, $R_5$ and $R_6$ are hydrogen; dl-1-methyl-3-(4,5,6,7-tetrahydrobenzo[b]thien-4-yl)urea.

9. The method according to claim 4 wherein the compound is the racemic mixture wherein X is oxygen, $n$ is 1, $R_1$ is hydrogen, $R_2$ is methoxy, $R_3$ is methyl, and $R_4$, $R_5$ and $R_6$ are hydrogen; dl-1-methoxy-1-methyl-3-(4,5,6,7-tetrahydrobenzo[b]thien-4-yl)urea.

10. The method according to claim 4 wherein the compound is the racemic mixture wherein X is oxygen, $n$ is 1, $R_1$ and $R_2$ are hydrogen, $R_3$ is ethyl, and $R_4$, $R_5$ and $R_6$ are hydrogen; dl-1-ethyl-3-(4,5,6,7-tetrahydrobenzo[b]thien-4-yl)urea.

11. The method according to claim 4 wherein the compound is the racemic mixture wherein X is oxygen, $n$ is 1, $R_1$ is hydrogen, $R_2$ is methoxy, and $R_3$, $R_4$, $R_5$ and $R_6$ are hydrogen; dl-1-methoxy-3-(4,5,6,7-tetrahydrobenzo[b]thien-4-yl)urea.

12. The method according to claim 4 wherein the compound is the racemic mixture wherein X is oxygen, $n$ is 1, $R_1$ is hydrogen, $R_2$ is hydroxy, $R_3$ is methyl, and $R_4$, $R_5$ and $R_6$ are hydrogen; dl-1-hydroxy-1-methyl-3-(4,5,6,7-tetrahydrobenzo[b]thien-4-yl)urea.

13. The method according to claim 4 wherein the compound is the racemic mixture wherein X is oxygen, $n$ is 1, $R_1$ is hydrogen; $R_2$ is hydroxy, and $R_3$, $R_4$, $R_5$ and R₆ are hydrogen; dl-1-hydroxy-3-(4,5,6,7-tetrahydrobenzo[b]thien-4-yl)urea.

14. The method according to claim 4 wherein the compound is the racemic mixture wherein X is oxygen, n is 1, R₁ is hydrogen; R₂ is methoxymethyl, and R₃, R₄, R₅ and R₆ are hydrogen; dl-1-methoxymethyl-3-(4,5,6,7-tetrahydrobenzo[b]thien-4-yl)urea.

15. The method according to claim 4 wherein the compound is the racemic mixture wherein X is oxygen, n is 1, R₁ and R₂ are hydrogen, R₃ is 2-propynyl, and R₄, R₅ and R₆ are hydrogen; dl-1-(2-propynyl)-3-(4,5,6,7-tetrahydrobenzo[b]-thien-4yl)urea.

16. The method according to claim 4 wherein the compound is the racemic mixture wherein X is oxygen, n is 1, R₁ and R₂ are hydrogen, R₃ is allyl, and R₄, R₅ and R₆ are hydrogen; dl-1-allyl-3-(4,5,6,7-tetrahydrobenzo[b]thien-4-yl)urea.

17. The method according to claim 4 wherein the compound is the racemic mixture wherein X is oxygen, n is 1, R₁ and R₂ are hydrogen, R₃ is isopropyl, and R₄, R₅ and R₆ are hydrogen; dl-1-isopropyl-3-(4,5,6,7-tetrahydrobenzo[b]-thien-4yl)urea.

18. The method according to claim 4 wherein the compound is the racemic mixture wherein X is oxygen, n is 1, R₁ is hydrogen, R₂ and R₃ are methyl, and R₄, R₅ and R₆ are hydrogen; dl-1,1-dimethyl-3-(4,5,6,7-tetrahydrobenzo[b]thien-4-yl)urea.

19. The method according to claim 4 wherein the compound is the racemic mixture wherein X is oxygen, n is 2, R₁ and R₂ are hydrogen, R₃ is methyl, and R₄, R₅ and R₆ are hydrogen; dl-1-methyl-3-(5,6,7,8-tetrahydro-4H-cyclohepta-[b]thien-4-yl)urea.

20. The method according to claim 4 wherein the compound is the racemic mixture wherein X is oxygen, n is 2, R₁ and R₂ are hydrogen, R₃ is ethyl, and R₄, R₅ and R₆ are hydrogen; dl-1-ethyl-3-(5,6,7,8-tetrahydro-4H-cyclohepta-[b]thien-4-yl)urea.

21. The method according to claim 4 wherein the compound is the racemic mixture wherein X is oxygen, n is 2, and R₁, R₂, R₃, R₄, R₅ and R₆ are hydrogen; dl-5,6,7,8-tetrahydro-4H-cyclohepta[b]thien-4-ylurea.

22. The method according to claim 4 wherein the compound is the racemic mixture wherein X is oxygen, n is 2, R₁ is hydrogen, R₂ is methoxymethyl, and R₃, R₄, R₅ and R₆ are hydrogen; dl-1-methoxymethyl-3-(5,6,7,8-tetrahydro-4H-cyclohepta[b]thien-4-yl)urea.

23. A method for improving the feed efficiency and enhancing the growth rate of veterinary homothermic animals which comprises administering to said animals an effective amount of a compound selected from the group consisting of the dextrorotatory enantiomorph, the levorotatory enantiomorph, and the racemic mixture thereof of a compound of the formula:

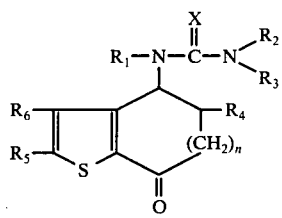

wherein X is oxygen or sulfur; n is the integer 1 or 2; R₁ is hydrogen or alkyl C₁–C₄; R₃ is selected from the group consisting of hydrogen, alkyl C₁–C₄, cycloalkyl C₃–C₆, allyl, 2-propynyl, benzyl and β-phenethyl; R₄ is hydrogen or alkyl C₁–C₄; R₅ is hydrogen, chloro, bromo or iodo; R₆ is hydrogen or alkyl C₁–C₄; R₂ is selected from the group consisting of the substituents listed in the following table:

hydrogen
alkyl C₁–C₈
cycloalkyl C₃–C₆
allyl
2-propynyl
hydroxy
alkoxy C₁–C₆
allyloxy
methoxymethyl
phenoxy
—CH₂—CH(OR)₂
—CH₂—CF₃
—CH₂—CN
—NH—CO₂R
—O—CH₂—CO₂H
—CO₂C₂H₅

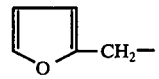

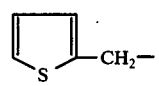

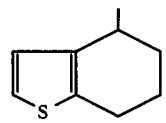

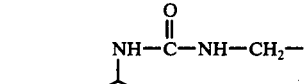

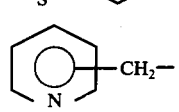

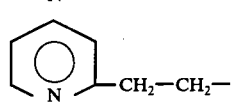

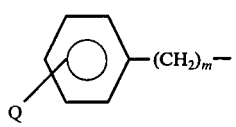

wherein R is alkyl C₁–C₄, m is 0, 1 or 2, and Q is selected from the group consisting of the substituents listed in the following table:

| m = 0 | m = 1 | m = 2 |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and R₂ and R₃ taken together with the associated N(itrogen) is selected from the group consisting of morpholino, piperidino, pyrrolidino, 4-(4-methoxyphenyl)-piperazino, 1,2,3,4-tetrahydroquinolino and the moiety of the formula:

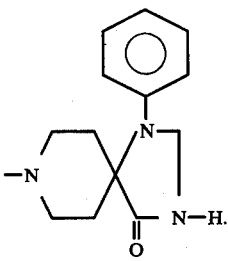

24. The method according to claim 21 wherein the compound is the racemic mixture wherein X is oxygen, n is 1, and $R_1$, $R_2$, $R_3$, $R_4$, $R_5$ and $R_6$ are hydrogen; dl-4,5,6,7-tetrahydro-7-oxobenzo[b]thien-4-ylurea.

25. The method according to claim 23 wherein the compound is the dextrorotatory enantiomorph wherein X is oxygen, n is 1, and $R_1$, $R_2$, $R_3$, $R_4$, $R_5$ and $R_6$ are hydrogen; d-4,5,6,7-tetrahydro-7-oxobenzo[b]thien-4-ylurea.

26. The method according to claim 23 wherein the compound is the levorotatory enantiomorph wherein X is oxygen, n is 1, and $R_1$, $R_2$, $R_3$, $R_4$, $R_5$ and $R_6$ are hydrogen; 1-4,5,6,7-tetrahydro-7-oxobenzo[b]thien-4-ylurea.

27. The method according to claim 23 wherein the compound is the racemic mixture wherein X is oxygen, n is 1, $R_1$ and $R_2$ are hydrogen, $R_3$ is methyl, and $R_4$, $R_5$ and $R_6$ are hydrogen; dl-1-methyl-3-(4,5,6,7tetrahydro-7-oxobenzo[b]-thien-4-yl)urea.

28. The method according to claim 23 wherein the compound is the racemic mixture wherein X is oxygen, n is 1, $R_1$ and $R_2$ are hydrogen, $R_3$ is ethyl, and $R_4$, $R_5$ and $R_6$ are hydrogen; dl-1-ethyl-3-(4,5,6,7-tetrahydro-7-oxobenzo[b]-thien-4-yl)urea.

29. The method according to claim 23 wherein the compound is the racemic mixture wherein X is oxygen, n is 1, $R_1$ is hydrogen, $R_2$ is methoxymethyl, and $R_3$, $R_4$, $R_5$ and $R_6$ are hydrogen; dl-1-methoxymethyl-3-(4,5,6,7-tetrahydro-oxobenzo[b]thien-4-yl)urea.

30. The method according to claim 23 wherein the compound is the racemic mixture wherein X is oxygen, n is 1, $R_1$ and $R_2$ are hydrogen, $R_3$ is 2-propynyl, and $R_4$, $R_5$ and $R_6$ are hydrogen; dl-1-(2-propynyl)-3-(4,5,6,7-tetrahydro-7-oxobenzo[b]thien-4-yl)urea.

31. The method according to claim 23 wherein the compound is the racemic mixture wherein X is oxygen, n is 1, $R_1$ and $R_2$ are hydrogen, $R_3$ is allyl, and $R_4$, $R_5$, and $R_6$ are hydrogen; dl-1-allyl-3-(4,5,6,7-tetrahydro-7-oxobenzo[b]thien-4-yl)urea.

32. The method according to claim 23 wherein the compound is the racemic mixture wherein X is oxygen, n is 1, $R_1$ is hydrogen, $R_2$ is methoxy, $R_3$ is methyl, and $R_4$, $R_5$, and $R_6$ are hydrogen, dl-1-methoxy-1-methyl-3-(4,5,6,7-tetrahydro-7-oxobenzo[b]thien-4-yl)urea.

33. The method according to claim 23 wherein the compound is the racemic mixture wherein X is oxygen, n is 1, $R_1$ is hydrogen, $R_2$ is hydroxy and $R_3$, $R_4$, $R_5$ and $R_6$ are hydrogen; dl-1-hydroxy-3(4,5,6,7-tetrahydro-7-oxobenzo[b]thien-4-yl)urea.

34. The method according to claim 23 wherein the compound is the racemic mixture wherein X is oxygen, n is 1, $R_1$ is hydrogen, $R_2$ is hydroxy, $R_3$ is methyl, and $R_4$, $R_5$ and $R_6$ are hydrogen; dl-1-hydroxy-1-methyl-3-(4,5,6,7-tetrahydro-7-oxobenzo[b]thien-4-yl)urea.

35. The method according to claim 23 wherein the compound is the racemic mixture wherein X is oxygen, n is 1, $R_1$ is hydrogen, $R_2$ is methoxy, and $R_3$, $R_4$, $R_5$ and $R_6$ are hydrogen; dl-1-methoxy-3-(4,5,6,7-tetrahydro-7-oxobenzo[b]thien-4yl)urea.

36. The method according to claim 23 wherein the compound is the racemic mixture wherein X is oxygen, n is 1, $R_1$ is hydrogen, $R_2$ and $R_3$ are methyl, and $R_4$, $R_5$ and $R_6$ are hydrogen; dl-1,1-dimethyl-3-(4,5,6,7-tetrahydro-7-oxobenzo-[b]thien-4-yl)urea.

37. The method according to claim 23 wherein the compound is the racemic mixture wherein X is oxygen, n is 1, $R_1$ and $R_2$ are hydrogen, $R_3$ is isopropyl, and $R_4$, $R_5$ and $R_6$ are hydrogen; dl-1-isopropyl-3-(4,5,6,7-tetrahydro-7-oxobenzo[b]thien-4-yl)urea.

38. The method according to claim 23 wherein the compound is the levorotatory enantiomorph wherein X is oxygen, n is 2, and $R_1$, $R_2$, $R_3$, $R_4$, $R_5$ and $R_6$ are hydrogen; 1-5,6,7,8-tetrahydro-8-oxo-4H-cyclohepta[b]thien-4-ylurea.

39. The method according to claim 23 wherein the compound is the racemic mixture wherein X is oxygen, n is 2, and $R_1$, $R_2$, $R_3$, $R_4$, $R_5$ and $R_6$ are hydrogen; dl-5,6,7,8-tetrahydro-8-oxo-4H-cyclohepta[b]thien-4ylurea.

40. A method for improving the feed efficiency and enhancing the growth rate of veterinary homothermic animals which comprises administering to said animals an effective amount of a compound selected from the group consisting of the cis-dextrorotatory enantiomorph, the cis-levorotatory enantiomorph, the racemic mixture of the cis-enantiomorphs, the trans-dextrorotatory enantiomorph, the trans-levortatory enantiomorph, and the racemic mixture of the trans-enantiomorphs of a compound of the formula:

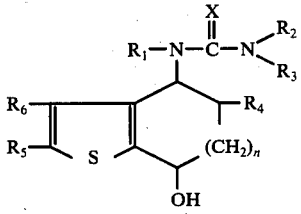

wherein X is oxygen or sulfur; n is the integer 1 or 2; $R_1$ is hydrogen or alkyl $C_1$–$C_4$; $R_3$ is selected from the group consisting of hydrogen, alkyl $C_1$–$C_4$, cycloalkyl $C_3$–$C_6$, allyl, 2-propynyl, benzyl and β-phenethyl; $R_4$ is hydrogen or alkyl $C_1$–$C_4$; $R_5$ is hydrogen, chloro, bromo or iodo; $R_6$ is hydrogen or alkyl $C_1$–$C_4$; $R_2$ is selected from the group consisting of the substituents listed in the following table:

hydrogen
alkyl $C_1$—$C_8$
cycloalkyl $C_3$—$C_6$
allyl
2-propynyl
hydroxy
alkoxy $C_1$—$C_6$
allyloxy
methoxymethyl
phenoxy
—$CH_2$—$CH(OR)_2$
—$CH_2$—$CF_3$
—$CH_2$—CN
—NH—$CO_2R$
—O—$CH_2$—$CO_2H$
—$CO_2C_2H_5$ -continued

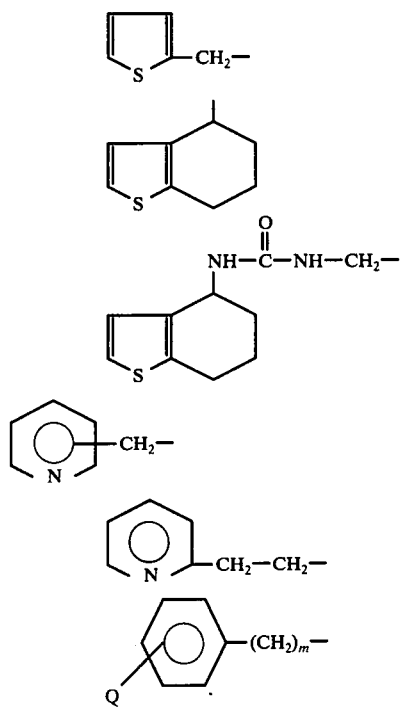

wherein R is alkyl $C_1$–$C_4$, $m$ is 0, 1 or 2, and Q is selected from the group consisting of the substituents listed in the following table:

| m = 0 | m = 1 | m = 2 |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and $R_2$ and $R_3$ taken together with the associated N(itrogen) is selected from the group consisting of morpholino, piperidino, pyrrolidino, 4-(4-methoxyphenyl)-piperazino, 1,2,3,4-tetrahydroquinolino and the moiety of the formula:

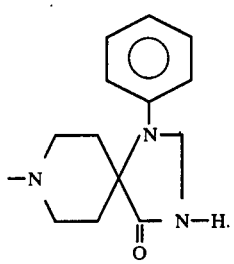

41. The method according to claim 40 wherein the compound is the cis-racemic mixture wherein X is oxygen, $n$ is 1, and $R_1$, $R_2$, $R_3$, $R_4$, $R_5$ and $R_6$ are hydrogen; dl-cis-4,5,6,7-tetrahydro-7-hydroxybenzo[b]thien-4-ylurea.

42. The method according to claim 40 wherein the compound is the trans-racemic mixture wherein X is oxygen, $n$ is 1, and $R_1$, $R_2$, $R_3$, $R_4$, $R_5$ and $R_6$ are hydrogen; dl-trans-4,5,6,7-tetrahydro-7-hydroxybenzo[b]thien-4-ylurea.

43. The method according to claim 40 wherein the compound is the cis-dextrorotatory enantiomorph wherein X is oxygen, $n$ is 1, and $R_1$, $R_2$, $R_3$, $R_4$, $R_5$ and $R_6$ are hydrogen; d-cis-4,5,6,7-tetrahydro-7-hydroxybenzo[b]thien-4-ylurea.

44. The method according to claim 40 wherein the compound is the cis-levorotatory enantiomorph wherein X is oxygen, $n$ is 1, and $R_1$, $R_2$, $R_3$, $R_4$, $R_5$ and $R_6$ are hydrogen; l-cis-4,5,6,7-tetrahydro-7-hydroxybenzo[b]thien-4ylurea.

45. The method according to claim 40 wherein the compound is the trans-dextrorotatory enantiomorph wherein X is oxygen, $n$ is 1, and $R_1$, $R_2$, $R_3$, $R_4$, $R_5$ and $R_6$ are hydrogen; d-trans-4,5,6,7-tetrahydro-7-hydroxybenzo[b]thien-4-ylurea.

46. The method according to claim 40 wherein the compound is the trans-levorotatory enantiomorph wherein X is oxygen, $n$ is 1, and $R_1$, $R_2$, $R_3$, $R_4$, $R_5$ and $R_6$ are hydrogen; l-trans-4,5,6,7-tetrahydro-7-hydroxybenzo[b]thien-4-ylurea.

47. The method according to claim 40 wherein the compound is the cis-racemic mixture wherein X is oxygen, $n$ is 1, $R_1$ and $R_2$ are hydrogen, $R_3$ is methyl, and $R_4$, $R_5$ and $R_6$ are hydrogen; dl-cis-1-methyl-3-(4,5,6,7-tetrahydro-7-hydroxybenzo[b]thien-4-yl)urea.

48. The method according to claim 40 wherein the compound is the trans-racemic mixture wherein X is oxygen, $n$ is 1, $R_1$ and $R_2$ are hydrogen, $R_3$ is methyl, and $R_4$, $R_5$ and $R_6$ are hydrogen; dl-trans-1-methyl-3-(4,5,6,7-tetrahydro-7-hydroxybenzo[b]thien-4-yl)urea.

49. The method according to claim 40 wherein the compound is the cis-racemic mixture wherein X is oxygen, $n$ is 1, $R_1$ and $R_2$ are hydrogen, $R_3$ is ethyl, and $R_4$, $R_5$ and $R_6$ are hydrogen; dl-cis-1-ethyl-3-(4,5,6,7-tetrahydro-7-hydroxybenzo[b]thien-4-yl)urea.

50. The method according to claim 40 wherein the compound is the trans-racemic mixture wherein X is oxygen, $n$ is 1, $R_1$ and $R_2$ are hydrogen, $R_3$ is ethyl, and $R_4$, $R_5$ and $R_6$ are hydrogen; dl-trans-1-ethyl-3-(4,5,6,7-tetrahydro-7-hydroxybenzo[b]thien-4-yl)urea.

51. The method according to claim 40 wherein the compound is the cis-racemic mixture wherein X is oxygen, $n$ is 1, $R_1$ is hydrogen, $R_2$ and $R_3$ are methyl, and $R_4$, $R_5$ and $R_6$ are hydrogen; dl-cis-1,1,-dimethyl-3-(4,5,6,7-tetrahydro-7-hydroxybenzo[b]thien-4yl)urea.

52. The method according to claim 40 wherein the compound is the trans-racemic mixture wherein X is oxygen, $n$ is 1, $R_1$ is hydrogen, $R_2$ and $R_3$ are methyl, and $R_4$, $R_5$ and $R_6$ are hydrogen; dl-trans-1,1-dimethyl-3-(4,5,6,7-tetrahydro-7-hydroxybenzo[b]thien-4yl)urea.

53. The method according to claim 40 wherein the compound is the cis-racemic mixture wherein X is oxygen, $n$ is 1, $R_1$ is hydrogen, $R_2$ is methoxymethyl, and $R_3$, $R_4$, $R_5$ and $R_6$ are hydrogen; dl-cis-1-methoxymethyl-3-(4,5,6,7-tetrahydro-7-hydroxybenzo[b]thien-4-yl)urea.

54. The method according to claim 40 wherein the compound is the trans-racemic mixture wherein X is oxygen, $n$ is 1, $R_1$ is hydrogen, $R_2$ is methoxymethyl, and $R_3$, $R_4$, $R_5$ and $R_6$ are hydrogen; dl-trans-1-methoxymethyl-3-(4,5,6,7-tetrahydro-7-hydroxybenzo[b]thien-4-yl)urea.

55. The method according to claim 40 wherein the compound is the cis-racemic mixture wherein X is oxygen, $n$ is 1, $R_1$ and $R_2$ are hydrogen, $R_3$ is isopropyl, and $R_4$, $R_5$ and $R_6$ are hydrogen; dl-cis-1-isopropyl-3-(4,5,6,7-tetrahydro-7-hydroxybenzo[b]thien-4-yl)urea.

56. The method according to claim 40 wherein the compound is the trans-racemic mixture wherein X is oxygen, n is 1, $R_1$ and $R_2$ are hydrogen, $R_3$ is isopropyl, and $R_4$, $R_5$ and $R_6$ are hydrogen; dl-trans-1-isopropyl-3-(4,5,6,7-tetrahydro-7-hydroxybenzo[b]thien-4-yl)urea.

57. The method according to claim 40 wherein the compound is the cis-racemic mixture wherein X is oxygen, n is 1, $R_1$ and $R_2$ are hydrogen, $R_3$ is 2-propynyl, and $R_4$, $R_5$ and $R_6$ are hydrogen; dl-cis-1-(2-propynyl)-3-(4,5,6,7-tetrahydro-7-hydroxybenzo[b]thien-4-yl)urea.

58. The method according to claim 40 wherein the compound is the trans-racemic mixture wherein X is oxygen, n is 1, $R_1$ and $R_2$ are hydrogen, $R_3$ is 2-propynyl, and $R_4$, $R_5$ and $R_6$ are hydrogen; dl-trans-1-(2-propynyl)-3-(4,5,6,7-tetrahydro-7-hydroxybenzo[b]thien-4-yl)urea.

59. The method according to claim 40 wherein the compound is the cis-racemic mixture wherein X is oxygen, n is 1, $R_1$ and $R_2$ are hydrogen, $R_3$ is allyl, and $R_4$, $R_5$ and $R_6$ are hydrogen; dl-cis-1-allyl-3-(4,5,6,7-tetrahydro-7-hydroxybenzo[b]thien-4-yl)urea.

60. The method according to claim 40 wherein the compound is the trans-racemic mixture wherein X is oxygen, n is 1, $R_1$ and $R_2$ are hydrogen, $R_3$ is allyl, and $R_4$, $R_5$ and $R_6$ are hydrogen; dl-trans-1-allyl-3-(4,5,6,7-tetrahydro-7-hydroxybenzo[b]thien-4-yl)urea.

61. The method according to claim 40 wherein the compound is the cis-racemic mixture wherein X is oxygen, n is 1, $R_1$ is hydrogen, $R_2$ is methoxy, and $R_3$, $R_4$, $R_5$ and $R_6$ are hydrogen; dl-cis-1-methoxy-3-(4,5,6,7-tetrahydro-7-hydroxybenzo[b]thien-4-yl)urea.

62. The method according to claim 40 wherein the compound is the trans-racemic mixture wherein X is oxygen, n is 1, $R_1$ is hydrogen, $R_2$ is methoxy, and $R_3$, $R_4$, $R_5$ and $R_6$ are hydrogen; dl-trans-1-methoxy-3-(4,5,6,7-tetrahydro-7-hydroxybenzo[b]thien-4-yl)urea.

63. The method according to claim 40 wherein the compound is the cis-racemic mixture wherein X is oxygen, n is 1, $R_1$ is hydrogen, $R_2$ is methoxy, $R_3$ is methyl, and $R_4$, $R_5$ and $R_6$ are hydrogen; dl-cis-1-methoxy-1-methyl-3-(4,5,6,7-tetrahydro-7-hydroxybenzo[b]thien-4-yl)urea.

64. The method according to claim 40 wherein the compound is the trans-racemic mixture wherein X is oxygen, n is 1, $R_1$ is hydrogen, $R_2$ is methoxy, $R_2$ is methoxy, $R_3$ is methyl, and $R_4$, $R_5$ and $R_6$ are hydrogen; dl-trans-1-methoxy-1-methyl-3-(4,5,6,7-tetrahydro-7-hydroxybenzo[b]thien-4-yl)urea.

65. The method according to claim 40 wherein the compound is the cis-racemic mixture wherein X is oxygen, n is 1, $R_1$ is hydrogen, $R_2$ is hydroxy, and $R_3$, $R_4$, $R_5$ and $R_6$ are hydrogen; dl-cis-1-hydroxy-3-(4,5,6,7-tetrahydro-7-hydroxybenzo[b]thien-4-yl)urea.

66. The method according to claim 40 wherein the compound is the trans-racemic mixture wherein X is oxygen, n is 1, $R_1$ is hydrogen, $R_2$ is hydroxy, and $R_3$, $R_4$, $R_5$ and $R_6$ are hydrogen; dl-trans-1-hydroxy-3-(4,5,6,7-tetrahydro-7-hydroxybenzo[b]thien-4-yl)urea.

67. The method according to claim 40 wherein the compound is the cis-racemic mixture wherein X is oxygen, n is 1, $R_1$ is hydrogen, $R_2$ is hydroxy, $R_3$ is methyl, and $R_4$, $R_5$ and $R_6$ are hydrogen; dl-cis-1-hydroxy-1-methyl-3-(4,5,6,7-tetrahydro-7-hydroxybenzo[b]thien-4-yl)urea.

68. The method according to claim 40 wherein the compound is the trans-racemic mixture wherein X is oxygen, n is 1, $R_1$ is hydrogen, $R_2$ is hydroxy, $R_3$ is methyl, and $R_4$, $R_5$ and $R_6$ are hydrogen; dl-trans-1-hydroxy-methyl-3-(4,5,6,7-tetrahydro-7-hydroxybenzo[b]thien-4yl)urea.

69. The method according to claim 40 wherein the compound is the cis-dextrorotatory enantiomorph wherein X is oxygen, n is 2, and $R_1$, $R_2$, $R_3$, $R_4$ $R_5$ and $R_6$ are hydrogen; d-cis-5,6,7,8-tetrahydro-8-hydroxy-4H-cyclohepta[b]thien-4-ylurea.

70. The method according to claim 40 wherein the compound is the cis-levorotatory enantiomorph wherein X is oxygen, n is 2, and $R_1$, $R_2$, $R_3$, $R_4$, $R_5$ and $R_6$ are hydrogen; l-cis-5,6,7,8-tetrahydro-8-hydroxy-4H-cyclohepta[b]thien-4-ylurea.

71. The method according to claim 40 wherein the compound is the cis-racemic mixture wherein X is oxygen, n is 2, and $R_1$, $R_2$, $R_3$, $R_4$, $R_5$ and $R_6$ are hydrogen; dl-cis-5,6,7,8-tetrahydro-8-hydroxy-4H-cyclohept[b]thien-4-ylurea.

72. The method according to claim 40 wherein the compound is the trans-dextrorotatory enantiomorph wherein X is oxygen, n is 2, and $R_1$, $R_2$, $R_3$, $R_4$, $R_5$ and $R_6$ are hydrogen; d-trans-5,6,7,8-tetrahydro-8-hydroxy-4H-cyclohepta[b]thien-4-ylurea.

73. The method according to claim 40 wherein the compound is the trans-levorotatory enantiomorph wherein X is oxygen, n is 2, and $R_1$, $R_2$, $R_3$, $R_4$, $R_5$ and $R_6$ are hydrogen; l-trans-5,6,7,8-tetrahydro-8-hydroxy-4H-cyclohepta[b]thien-4-ylurea.

74. The method according to claim 40 wherein the compound is the trans-racemic mixture wherein X is oxygen, n is 2, and $R_1$, $R_2$, $R_3$, $R_4$, $R_5$ and $R_6$ are hydrogen; dl-trans-5,6,7,8-tetrahydro-8-hydroxy-4H-cyclohepta[b]thien-4-ylurea.

75. An animal feed composition for improving feed efficiency and enhancing the growth rate of poultry, furbearing and farm animals comprising, a nutritionally balanced animal feed containing from 0.0001% to 0.08% by weight of a compound selected from the group consisting of those of the formulae:

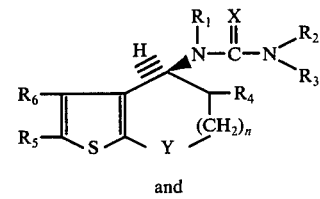

and

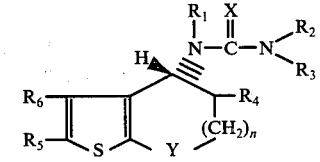

wherein X is oxygen or sulfur; n is the integer 1 or 2; Y is a divalent radical selected from the group consisting of those of the formulae:

$R_1$ is hydrogen or alkyl $C_1$–$C_4$; $R_3$ is selected from the group consisting of hydrogen, alkyl $C_1$–$C_4$, cycloalkyl $C_3$–$C_6$, allyl, 2-propynyl, benzyl and β-phenethyl; $R_4$ is hydrogen or alkyl $C_1$–$C_4$; $R_5$ is hydrogen, chloro, bromo or iodo; $R_6$ is hydrogen or alkyl $C_1$-$C_4$; $R_2$ is selected from the group consisting of the substituents listed in the following table:

```
hydrogen
alkyl C₁—C₈
cycloalkyl C₃—C₆
allyl
2-propynyl
hydroxy
alkoxy C₁—C₆
allyloxy
methoxymethyl
   phenoxy
   —CH₂—CH(OR)₂
   —CH₂—CF₃
   —CH₂—CN
   —NH—CO₂R
   —O—CH₂—CO₂H
   —CO₂C₂H₅
```

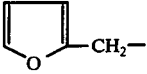

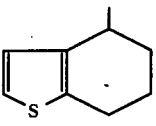

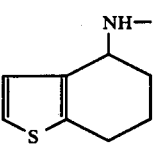

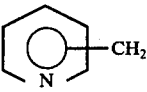

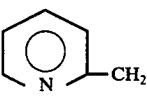

wherein R is alkyl $C_1$-$C_4$; $m$ is 0, 1 or 2, and Q is selected from the group consisting of the substituents listed in the following table:

| m = 0 | m = 1 | m = 2 |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and $R_2$ and $R_3$ taken together with the associated N(itrogen) is selected from the group consisting of morpholino, piperidino, pyrrolidino, 4-(4-methoxyphenyl)-piperazino, 1,2,3,4-tetrahydroquinolino and the moiety of the formula:

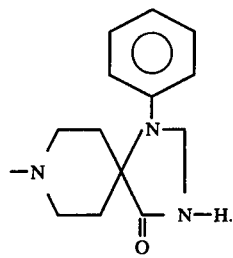

76. An animal feed premix for enhancing the growth rate of poultry, fur-bearing and farm animals comprising, from about 70% to 99% by weight of an edible carrier and from about 1% to 30% by weight of, a compound selected from the group consisting of those of the formulae:

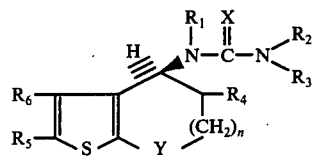

and

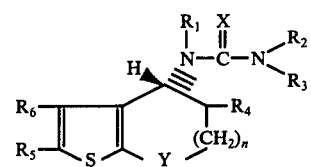

wherein X is oxygen or sulfur; $n$ is the integer 1 or 2; Y is a divalent radical selected from the group consisting of those of the formulae:

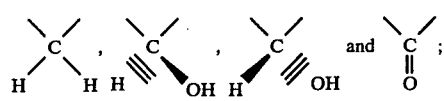

$R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and $\beta$-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

```
hydrogen
alkyl C₁—C₈
cycloalkyl C₃—C₆
allyl
2-propynyl
hydroxy
alkoxy C₁—C₆
allyloxy
methoxymethyl
phenoxy
—CH₂—CH(OR)₂
—CH₂—CF₃
—CH₂—CN
—NH—CO₂R
—O—CH₂—CO₂H
—CO₂C₂H₅
```

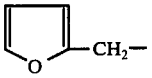

-continued

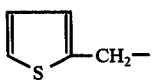

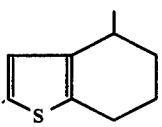

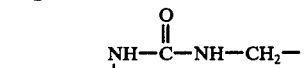

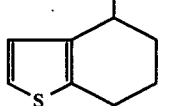

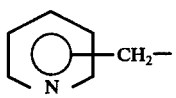

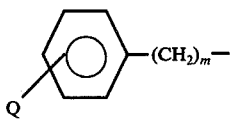

wherein R is alkyl $C_1$–$C_4$, m is 0, 1 and 2, and Q is selected from the group consisting of the substituents listed in the following table:

| m = 0 | m = 1 | m = 2 |
|---|---|---|
| 4-nitro | hydrogen | hydrogen |
| 3- or 4-methoxy | 4-chloro | |
| 4-ethoxy | 4-methoxy | |
| 4-chloro | | |
| 4-butoxy | | |
| 2,4-dimethyl | | |
| 2,4-dichloro | | |
| 2,5-dimethoxy | | | and $R_2$ and $R_3$ taken together with the associated N(itrogen) is selected from the group consisting of morpholino, piperidino, pyrrolidino, 4-(4-methoxyphenyl)-piperazino, 1,2,3,4-tetrahydroquinolino and the moiety of the formula:

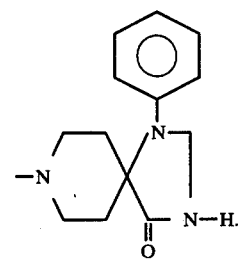

* * * * *

UNITED STATES PATENT AND TRADEMARK OFFICE
CERTIFICATE OF CORRECTION

PATENT NO. : 4,036,979
DATED : July 19, 1977
INVENTOR(S) : Goro Asato

It is certified that error appears in the above—identified patent and that said Letters Patent are hereby corrected as shown below:

IN CLAIM 3:

Delete lines 34 through 63.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*

UNITED STATES PATENT OFFICE
CERTIFICATE OF CORRECTION

Patent No. 4,036,979        Dated July 19, 1977

Inventor(s) Goro Assato

It is certified that error appears in the above-identified patent and that said Letters Patent are hereby corrected as shown below:

Col. 73, line 13, Claim 24 should read--

24. The method according to claim 23 wherein the compound is the racemic mixture wherein X is oxygen, n is 1, and $R_1$, $R_2$, $R_3$, $R_4$, $R_5$ and $R_6$ are hydrogen; dl-4,5,6,7-tetrahydro-7-oxobenzo[b]thien-4-ylurea --.

Signed and Sealed this

Twentieth Day of August 1985

[SEAL]

Attest:

DONALD J. QUIGG

Attesting Officer    Acting Commissioner of Patents and Trademarks